United States Patent [19]

Mattson et al.

[11] Patent Number: 5,559,018
[45] Date of Patent: Sep. 24, 1996

[54] INVIABLE PHAGES, THEIR PRODUCTION AND DNA THEREOF

[76] Inventors: Thomas L. Mattson, 19, rue de la Filature, 1227 Carouge, Geneva; Richard Epstein, 56 avenue Communes-Reunies, 1212 Grand Lancy, Geneva, both of Switzerland

[21] Appl. No.: 946,033

[22] Filed: Sep. 15, 1992

Related U.S. Application Data

[63] Continuation of Ser. No. 662,498, Feb. 28, 1991, abandoned, which is a continuation of Ser. No. 233,681, Jan. 16, 1986, abandoned.

[30] Foreign Application Priority Data

Sep. 13, 1983 [GB] United Kingdom .................. 8324479

[51] Int. Cl.$^6$ ........................... C12N 15/00; C12N 15/63
[52] U.S. Cl. ................... 435/172.3; 435/235.1; 435/320.1; 935/31
[58] Field of Search ................... 435/69.1, 71.2, 435/91.1, 171.1, 172.3, 235, 236, 238, 239, 252.3–252.35, 320.1, 235.1; 536/23.7, 24.1; 935/31, 58, 73

[56] References Cited

U.S. PATENT DOCUMENTS

| | | | |
|---|---|---|---|
| 4,332,897 | 6/1982 | Nakano et al. | 435/172.3 |
| 4,348,478 | 9/1982 | Nakano et al. | 435/172.3 |
| 4,415,660 | 11/1983 | Goldstein | 435/172.3 |
| 4,460,689 | 7/1984 | Foor et al. | 435/172.3 |
| 4,845,031 | 7/1989 | Shub et al. | 435/68 |

OTHER PUBLICATIONS

Takahashi et al, Mol. Gen. Genet. 186: 497 (1982).
Blattner et al; Science 196: 161 (1977).
Bolivar et al; Gene 2: 95 (1977).
Christensen et al; in Bacteriophage $T_4$; Christensen et al (ed.), 1983, American Society for Microbiology, Washington, D.C., pp. 184–188.
Geiduschek et al; in Bacteriophage $T_4$; Chirstensen et al(ed.), 1983, American Society for Microbiology, Washington, D.C., pp. 189–192.
Casna et al; Gene 18: 297 (1982).
Mattson et al; J. Mol. Biol. 170: 343 (1983).
Mattson et al; J. Mol. Biol. 170: 357 (1983).
Young et al; J. Mol. Biol. 138: 423 (1980).
Maniatis et al, Molecular Cloning, A Laboratory Manual, 1982, Cold Spring Harbor Laboratory, Cold Spring Harbor, N.Y., pp. 76–78.

*Primary Examiner*—James Martinell
*Attorney, Agent, or Firm*—Foley & Lardner

[57] ABSTRACT

Inviable T4 phage-like particles capable of directing the expression of large non-T4 DNA fragments from T4 expression control sequences are produced. Thus, *E. coli* harboring pBR322 derivatives containing cloned T4 gene 23 DNA sequences were infected with T4 phage carrying a deletion of the denB gene. Homology-dependent recombination results in the production of inviable phage-like particles containing DNA molecules composed of multiple, tandemly repeated copies of entire plasmid molecules covalently linked to single copies of normal phage genes. The yield of these inviable particles, intially low, was increased by means of a reiterated infection process that involves the use of a cloned T4 origin of replication. When T4 gene 32 expression control sequences linked in proper orientation to a DNA sequence coding for the non-T4 protein β-galactosidase were also cloned in one such pBR322 derivative (pVH773), inviable phage particles capable of directing the synthesis of enzymatically active β-galactosidase were produced. The present process is applicable to other T-even bacterio-phages.

22 Claims, 20 Drawing Sheets

LINEAGE OF pVH691 AND pVH737

ALTERNATE PATHWAYS FOR PLASMID-PHAGE RECOMBINATION

LINEAGE OF pVH686

FIG. 9B

NUCLEOTIDE SEQUENCE OF pVH676:

```
114.00 kb    .10       .20       .30       .40       .50       .60
AGATCTTCTATCTCATTCATATTGTTCTCTATTCAATTGTTATTGGTTGTTATTGGATGGACT
TCTAGAGATTAGAGTATAACAGAGATAAGTTAACAATAACCAACAATAACCTACCTGA

.70       .80       .90       .100      .110      .120
TAGATTCATTATACCACGTTTAACGTGAAGCATTATACTCTATTACTGGAAGCCAGCTG
ATCTAAGTAATATGGTGCAAATTGCACTTCGTATATGAGATAATGACCTTCGGTCGAC

.130      .140      .150
CAGTTTTATCTGCTCAATATCATCAGGATTATCGAT
GTCAAAATAGACGAGTTATAGTAGTCCTAATAGCTA
                              114.15 kb
```

←P23

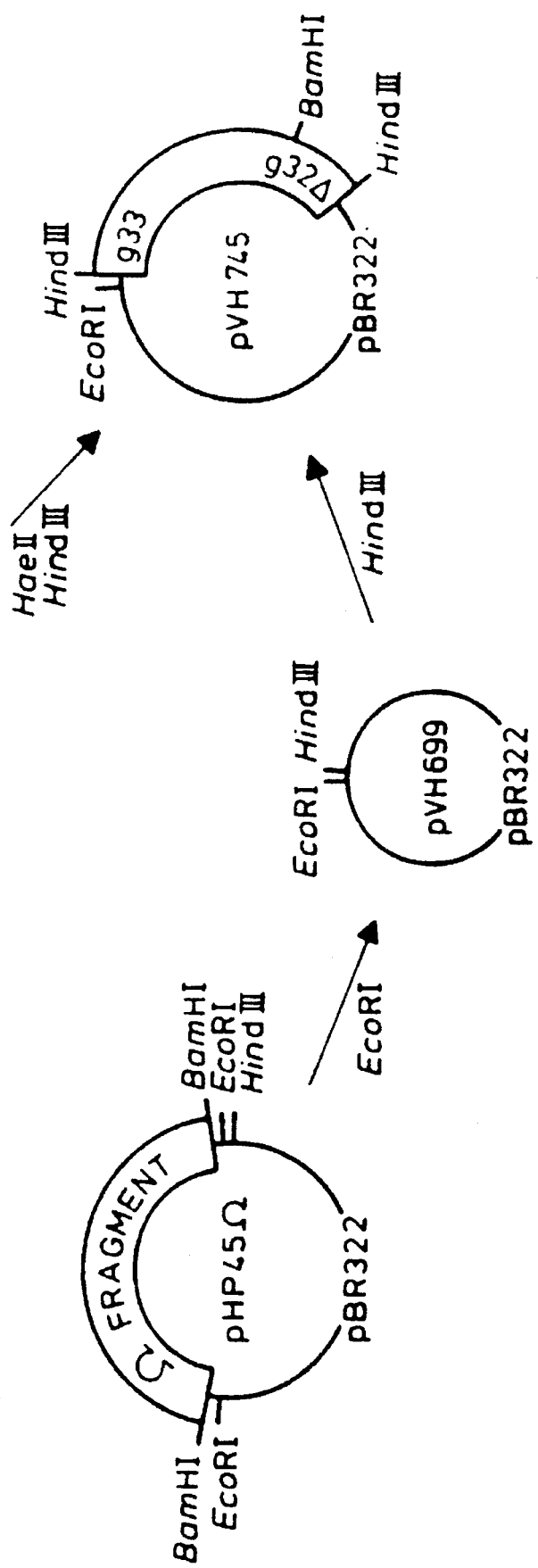
FIG. 12C   CONSTRUCTION OF PLASMID pVH745

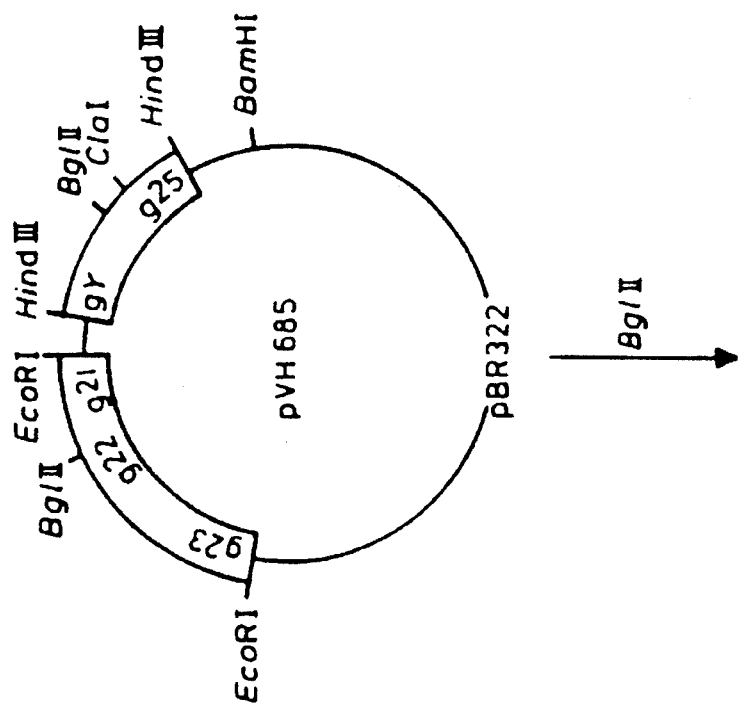
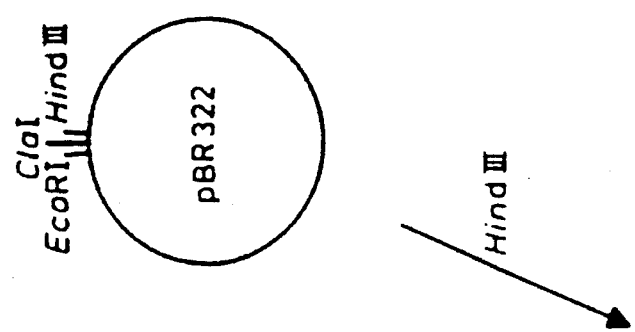
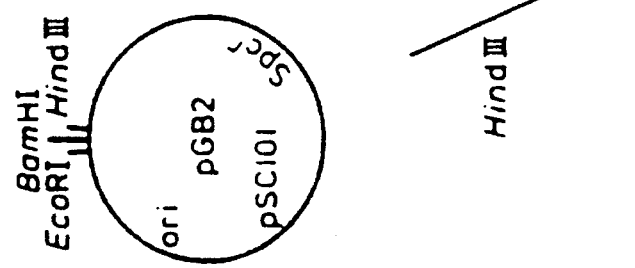
FIG. 13A

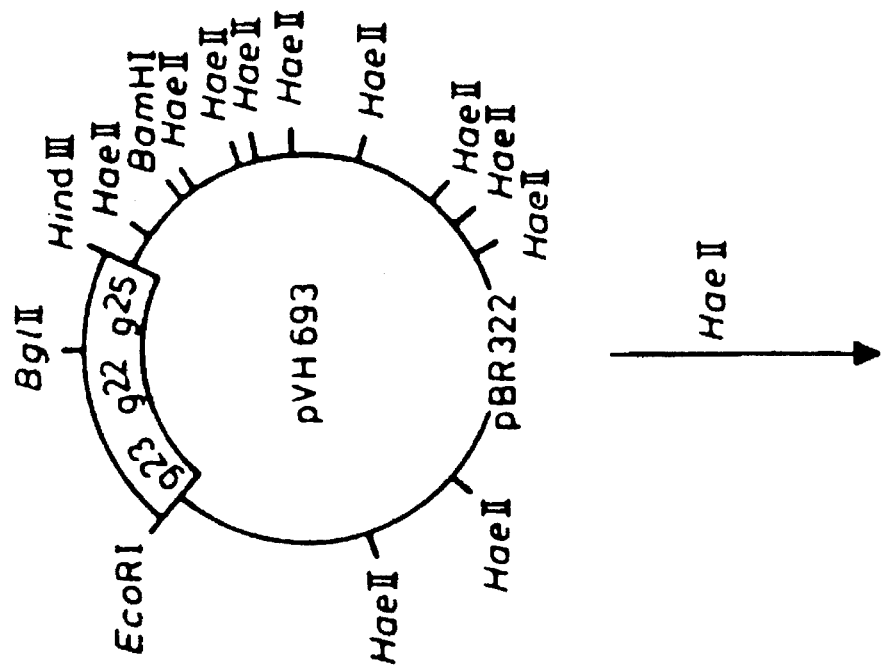
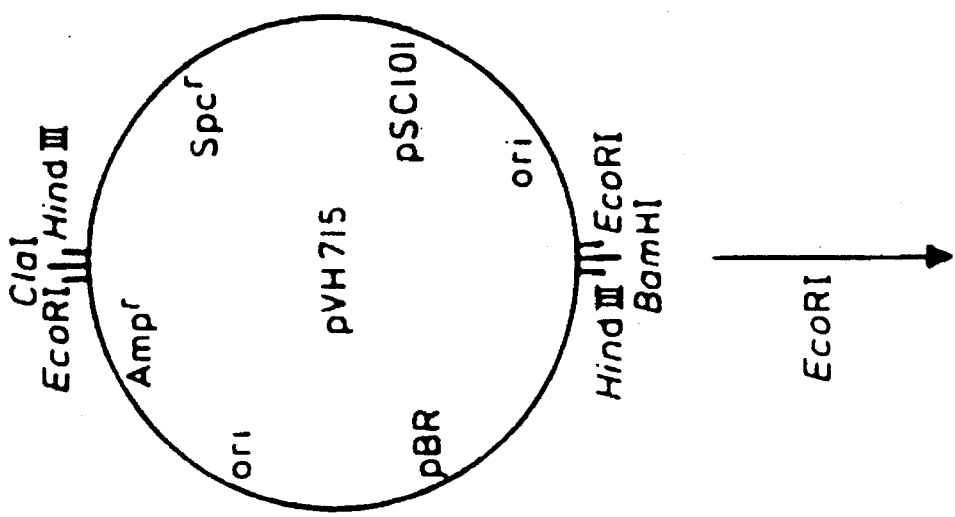
FIG. 13B

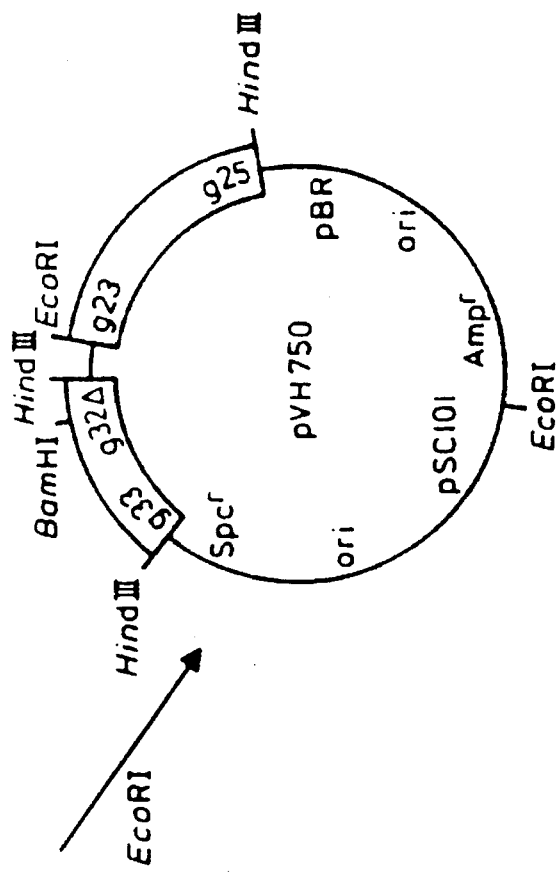
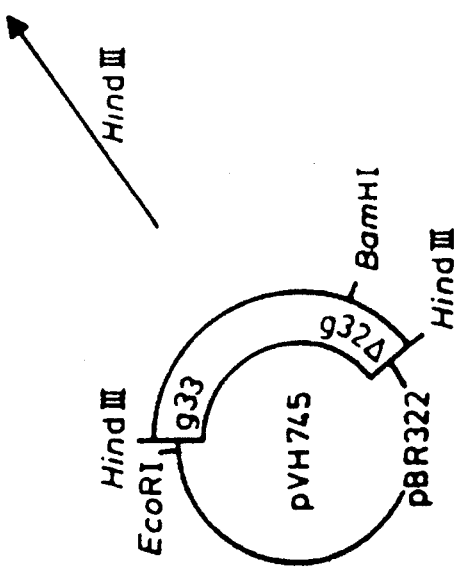
FIG. 13D
CONSTRUCTION OF PLASMID pVH750

INVIABLE PHAGES, THEIR PRODUCTION AND DNA THEREOF

This application is a continuation of U.S. application Ser. No. 07/662,498 filed Feb. 28, 1991, now abandoned; which is a continuation of Ser. No. 07/233,681 filed Jan. 16, 1986, now abandoned.

Bacteriophage T4, a member of the T-even group of *E. coli* bacteriophages, is currently used for the commercial production of enzymes (T4 DNA polymerase, T4 RNA ligase, T4 polynucleotide kinase) widely used in the field of Molecular Biology. This group of bacteriophages has other potentially useful properties. For example, N. J. Casna and D. A. Shub "Bacteriophage T4 as a generalized DNA-cloning vehicle" Gene 18: 297–307 (1982) have stated that their method for cloning DNA into T4 genomes is a general method of converting all of the cytosine residues of any particular piece of DNA into hydroxymethylcytosine residues. (Hydroxymethylcytosine and not cytosine is the normal constituent of T-even phage DNAs.) The study of hydroxymethylcytosine substituted DNA fragments could contribute to an understanding of the specificity of protein-DNA interactions. It has also been shown, (L. D. Simon, K. Tomczak and A. C. St. John "Bacteriophages inhibit degradation of abnormal proteins in *E. coli*" Nature (London) 275: 424–428 [1978]) that T4 infected cells provide an anti-protease environment for abnormal *E. coli* proteins. A T4 restriction fragment encoding an anti-protease activity has been cloned and used to increase the yield of a eukaryotic protein in *E. coli* (L. D. Simon, B. Randolf, N. Irwin and G. Binkowski "Stabilization of proteins by a bacteriophage T4 gene cloned in *Escherichia coli*" Proc. Natl. Acad. Sci. (USA) 80: 2059–2062 (1983), (L. D. Simon and R. B. Fay "T4 DNA fragment as a stabilizer for proteins expressed by cloned DNA" Eur. Pat. Appln. E.P. 72925).

These two examples of T-even bacteriophages characteristics suffice to show that the ability to clone and express foreign DNA in T-even bacteriophages may be useful. Methods currently used for the commercial exploitation of normal T4 phage particles should be easily adaptable to T-even phage particles containing foreign DNA sequences.

At present the largest piece of foreign DNA cloned into a T-even phage genome is a 203 base pair fragment of the *E. coli* lac operon (N. J. Casna and DNA. Shub op cit). This was done by an in vivo process that resembles or is identical to marker rescue recombination (infra) and results in a recombinant genome that can be packaged into a viable phage particle.

The ability to package a T-even genome containing foreign DNA into a viable phage particle is useful because the recombinant genome can be introduced into another bacteria by the normal infection process and propagated as a pure clone. However, the packaging of a recombinant genome containing a large segment of foreign DNA into a phage particle would rarely if ever result in a viable phage particle. That is, since a normal sized phage head can hold only a little more DNA than is in a normal sized phage genome the packaging of a large amount of foreign DNA would necessarily result in the deletion of an almost equal amount of phage DNA. Such phage particles would be inviable because essential phage genes are located in all regions of the phage genome.

Two classes of inviable phage particles containing foreign DNA have previously been indentified: G. G. Wilson, K. K. Y. Young and G. J. Edlin "High-frequency generalized transduction by bacteriophage T4" Nature (London) 280: 80–82 (1979). Both of these classes of phage particles are produced in very low yields, have not been propagated nor have they been physically separated from the vast majority of normal viable phage particles. One class of inviable phage particles contains DNA from the host chromosome and the other class contains only plasmid DNA. The plasmid DNA in these particles is in the form of tandem repeats and is not attached to either *E. coli* chromosomal DNA or to phage genomes (H. Takahashi and H. Saito "Mechanism of pBR322 transduction mediated by cytosine-substituting T4 Bacteriophage" Mol. gen. genet. 186: 497–500 (1982) and H. Takahashi and H. Saito "High-frequency transduction by cytosine-substituted T4 bacteriophage: Evidence for encapsulation and transfer of head-to tail concatemers" Plasmid 8: 29–35 (1982).

Thus the main problems in efficiently exploiting T-even bacteriophages for cloning and expressing specific predetermined foreign DNA sequences are essentially how to get large fragments of foreign DNA into phage genomes and how to progagate inviable phage particles containing these recombinants.

The invention provides a method of producing a population of inviable T-even bacteriophage particles or DNA thereof, said particles containing DNA of predetermined non-T-even base sequence, optionally under the control of a T-even expression control sequence, which method comprises infecting a host bacterium containing a replicon having such sequence with a T-even phage optionally carrying a mutation or combination of mutations which abolish all functions of the wild type denB gene, said replicon containing a DNA sequence homologous to a sequence in the phage DNA, provided that if the phage does not carry such mutation or combination of mutations the bacterium does not permit the phage wild type denB gene to function.

It will be appreciated that a combination of T-even expression control sequences may, if desired, be used.

In general terms this invention solves these problems by initially making a few inviable phage-like particles containing predetermined foreign DNA sequences cloned into specific regions of a phage chromosome and a much larger number of normal viable phage particles. These viable and inviable particles can then be used to reinfect fresh cells with both kinds of particles to increase the relative yield of the inviable particles containing the cloned DNA.

Preferably, use may be made in this invention of an unusual type of plasmid phage recombinant genome that is not known in the prior art. This type of recombinant has been identified and characterized and adapted to serve as a vehicle for cloning and expressing large predetermined fragments of foreign DNA in T-even infected cells. In this type of recombinant tandemly repeated copies of entire plasmid molecules may be added to individual phage chromosomes, that is, the product of the recombination may be a DNA molecule comprising multicopy sequences covalently linked to single copy sequences.

This new type of recombinant can be produced when there is DNA homology between the plasmid replicon and the infecting phage genomes if the denB gene of the phage is inactive. Although phage strains are usually employed that carry denB gene mutations, it is possible that bacterial strains exist or could be produced that block the phage denB gene functions. In this case one would not need to employ denB mutant phage strains.

A region of as little as 100 bases in duration could be employed; the precise duration is not critical and can be much larger. Thus, the importance to the invention of the presence of a region of homology between phage DNA and bacterial replicon must be emphasized to achieve good results.

The yield of the above type of recombinant molecule can also be significantly increased by using a reiterated process. This reiterated process involves using the inviable particles containing said recombinants to reinfect cells that can produce more of these recombinants. An essential element in this reiterated process is that cells infected with a non-viable particle containing one of the recombinants are also infected with a viable phage particle. With this reiterated process one can be guaranteed that at least one progeny particle out of five will be an inviable particle containing cloned DNA. Since each of the inviable particles contains a number of copies of the cloned DNA but only a single copy of the phage vector sequences, one will be able to produce a population of particles in which there are more copies of the cloned DNA than of normal phage genes. This is in contrast to other cloning vectors, where one has an equal number of copies of cloned and vector sequences. For this reiterated process it is highly desirable to include in the replicon to be cloned into a phage chromosome, a restriction fragment characterized as a functional T4 origin of replication.

The invention thus includes in another aspect a population of T-even phage particles containing at least 20% of inviable phages having a predetermined non-T-even base sequence. Preferably, in said inviable phases said predetermined non-T-even base sequence is in proper orientation to and under the control of a T-even expression control sequence.

Thus, the present invention generally solves the problems referred to above by providing at least one population of T-even phage and T-even phage-like particles in which a significant fraction of the total particles contain recombinant genomes in which, preferably, large amounts of predetermined non-phage DNA sequences are cloned into phage genomes. These recombinants can be used to express said foreign DNA sequences from designated phage expression control elements. The populations of phage-like particles of the invention are such as to enable injection of said recombinant genomes into bacterial strains.

The invention further provides an inviable T-even phage genome comprising a section having a predetermined non T-even base sequence cloned thereinto and in proper orientation to and under the control of a T-even expression control sequence.

In yet another aspect the invention includes a DNA sequence favouring autonomous replication of plasmid pBR322 in $E. coli$ when $E. coli$ is infected with T-even phage.

By virtue of this invention, it is possible to obtain substantial quantities of phage-like particles containing large amounts of predetermined non-phage DNA cloned into phage genomes. The DNA sequences, recombinant DNA molecules, mutant phage strains, populations of phage and phage-like particles and processes of this invention permit the replication and accumulation of recombinant genomes comprising large amounts of predetermined non-phage DNA cloned into phage genomes and the injection of said recombinant genomes into bacterial strains without the necessity of producing viable phage particles containing said recombinant genomes or of separating inviable phage-like particles containing said recombinant genomes from the viable phage particles. These populations of phage and phage-like particles, DNA sequences, recombinant DNA molecules and the processes of this invention therefore solve the problems which beset other known methods that might be capable of producing phage or phage-like populations containing large fragments of predetermined non-phage DNA sequences cloned into phage genomes.

As will be appreciated from the disclosure to follow, recombinant genomes in the populations of phage and phage-like particles of this invention are capable in appropriate hosts of expressing predetermined non-phage DNA sequences cloned into phage genomes from designated T-even expression control elements. The populations of phage and phage-like particles, DNA sequences, recombinant DNA molecules and mutant phage strains of this invention thus may be useful, either as produced in the host or after appropriate modification, in compositions and methods for improving the production of these products themselves and for use in the production of other similar populations of phage and phage-like particles capable of expressing particular DNA sequences of interest.

Reference will now be made to the drawings.

BRIEF DESCRIPTION OF THE DRAWINGS

FIGS. 12A–12C summarize the construction of plasmid pVH745.

FIGS. 13A–13D summarize the construction of plasmid pVH750.

Figure 1:
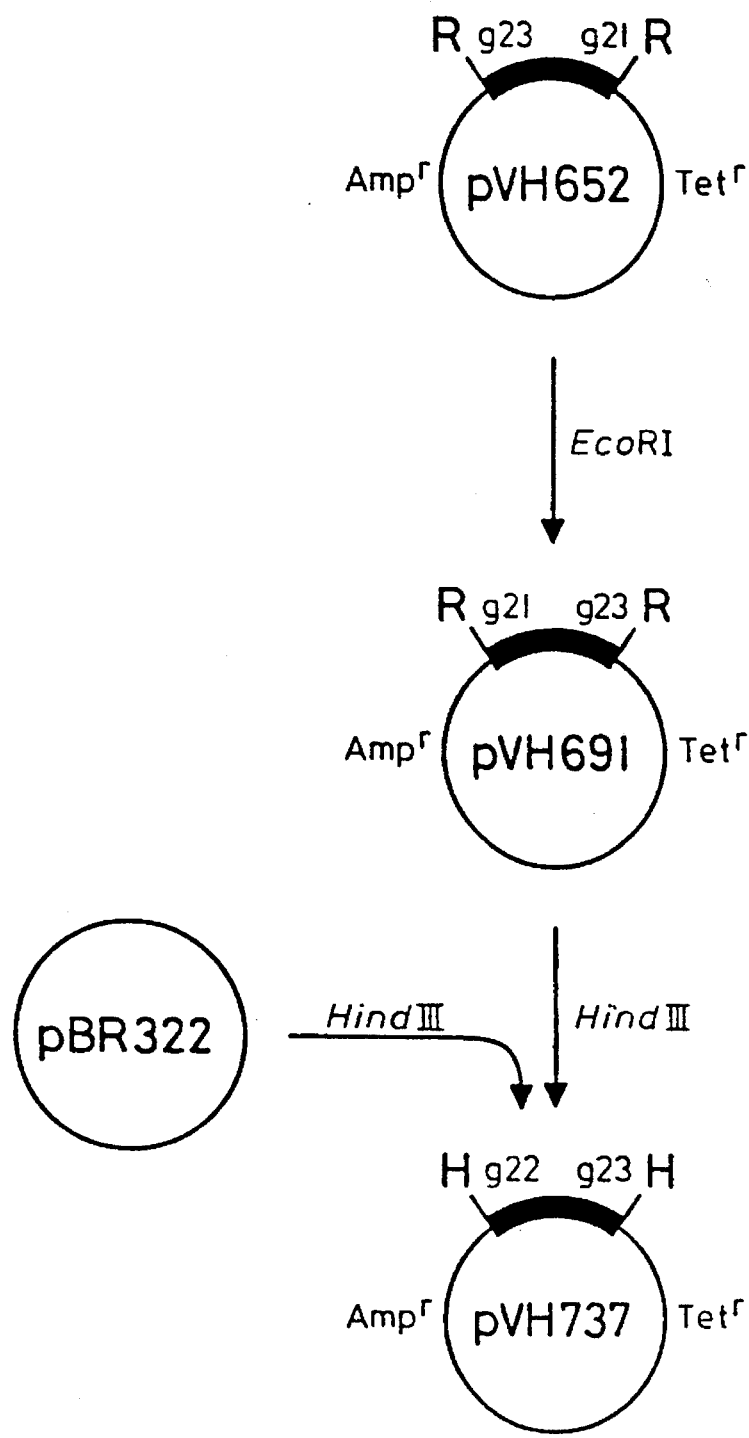
FIG. 1 summarizes the derivation of the chimeric plasmids pVH691 and pVH737.

The symbol P32 refers to the gene 32 promotor which is in the proper orientation for transcribing foreign DNA inserted into the BamHI restriction site.

In order that the invention herein described may be more fully understood, the following detailed description is set forth.

CHARACTERIZATION OF ELEMENTS OF THE INVENTION AND ILLUSTRATION OF TECHNIQUES

Starting Materials

Recombinant DNA molecules necessary for performing this invention can be constructed in vitro from a convenient E. coli double stranded DNA cloning vehicle chosen from among the derivatives of colE1-type plasmids, pACYC184, F, RSF1010 and RK2, but it is not limited to these plasmid types. The high copy number plasmid pBR322 may, of course, be used. Plasmids pVH691 and pVH737 (see below) are pBR322 derivatives containing DNA from the genes 21 to 23 region of the T4 genome. They were derived from plasmid pVH652 (E. T. Young, T. Mattson, G. Selzer, G. VanHouwe, A. Bolle and R. Epstein "Bacteriophage T4 gene transcription studied by hybridization to cloned restriction fragments". J. Mol. Biol. 138: 423–445 [1980]) according to methods well known in the art.

Plasmid pVH691, which contains a single T4 EcoR1 restriction fragment coding for T4 genes 21–23 was derived from plasmid pVH652 after EcoRI digestion and differs from pVH652 only in the orientation of the T4 inert. In pVH691, gene 23 is closer to the tetracycline resistant determinant than gene 21. Plasmid pVH737 was derived from plasmid pVH691 in the following manner.

Plasmid pBR322 and plasmid pVH691 DNAs (purified by Ethidium bromide—cesium chloride density gradient centrifugation of cleared lysates) were digested separately in TA buffer (33 mM tris-acetate, pH 7.9; 66 mM MgAc; 10 mm MgAc; 0.5mM DTT and 100 µg/ml BSA) at 37° C. with the restriction endonuclease enzyme HindIII (New England Biolabs), heated at 70° C. to inactivate the enzyme, mixed together and ligated at 15° C. with T4 DNA ligase (New England Biolabs). Ligation mixtures were transformed into E. coli C600 (a permissive strain for amber mutations).

Cells were prepared for transformation with plasmid DNA by the $CaCl_2$ method essentially as described by G. Selzer et al, "Construction and properties of recombinant plasmids containing the γII genes of bacteriophage T4", Molec. gen genet. 159:pp 301–309 (1978). Cells were grown at 37° C. in LB media to an absorbance $_{550}$ of 0.6–0.8, chilled, centrifuged, resuspended in one-half volume of 10 mM NaCl, centrifuged again and resuspended in one-tenth the original volume of 75 mM $CaCl_2$. The competent cells thus produced were either used directly or stored in small aliquots at −70° C. for subsequent use after adding 15 percent volume of glycerol. The competent cells were mixed with one-tenth volume or less of plasmid DNA, left for 30 minutes on ice, heated for two minutes at 42° C. and then returned to an ice bath for 40 minutes before adding 10 volumes of LB media (per liter: 10 g tryptone (Difco), 5 g yeast extract (Difco), 10 g NaCl, and 4.5 ml of 0.5N NaOH); supplemented with 0.1% (w/v) glucose. These transformed cells were then incubated at 37° C. for 1–2 hours before spreading on drug containing LA agar plates (LB media plus 15 g of Difco agar per liter) supplemented with 0.1% (w/v) glucose, 2.5 mM$CaCl_2$ and 20 µg/ml thymine.

After growth of the transformed cells on ampicillin-containing agar plates, individual colonies were tested for the presence of different markers in the T4 gene 21–23 region by standard marker rescue tests.

Thus, several colonies (containing only the markers expected for the HindIII restriction fragment that covers parts of gene 22 and gene 23) were genetically identified.

Plasmid DNA was prepared as described above from several of these colonies after single colony purification. These plasmid DNAs were analyzed by conventional recombinant DNA methodologies of restriction enzyme digestion and electrophoresis on agarose gels to identify plasmid pVH737 in which the orientation of the T4 DNA insert is that indicated in FIG. 1. The derivation of plasmids pVH691 and pVH737 is summarized in FIG. 1.

These techniques may also be employed in preparing recombinant plasmid molecules with other segments of T4 DNA. The recombinant DNA molecules constructed in vitro are then employed as described below to produce plasmid-phage recombinant genomes. Phage-like particles containing the plasmid-phage recombinant genomes are then used to characterize these recombinants.

Bacteriophage strains used in this invention were constructed by standard methods. Bacteriophage strains carrying multiple mutations were identified among the progeny phage produced in standard phage crosses done in CR63 according to procedures generally known in the art. Individual phage mutations used in the construction of the multiple mutants (42amN55, 56amE51, denAS112, 23amA489 and the denB gene deletion SAΔ9) are widely used mutations and are readily available from many different laboratories. Numerous other generally available mutations of each of these genes could equally well have been used for constructing mutant phage stocks in accordance with this invention. The alc gene mutation TB1 has not been previously described. It was isolated essentially as described by Snyder et al., "A gene of bacteriophage T4 whose produce prevents true late transcription of cytosine-containing T4 DNA", Proc. Nat. Acad. Sci. (USA), 73:pp 3098–3102 (1976), to isolate alc gene mutations. A quadruple mutant (23amA489–56amE51-denAS112-SaΔ9) was plated on a lawn of E. coli B834-pVH652, a strain non-permissive for amber mutations and lacking in the restriction and modification properties of *E. coli* K. strains. One of the phage plaques isolated from this plating on B834-pVH652 carried the mutation TB1, which is in the alc gene.

Identification of individual phage mutations in multiple mutant phage stocks The deletion SAΔ9 was detected in individual phage plaques by its acridine resistance phenotype in spot tests using CR63 plating bacteria and 1 μg/ml acriflavin in the bottom agar. denA mutant phage were identified first by their hydroxyurea (HU) sensitivity and then confirmed by a DNA-DNA hybridization test. The HU sensitivity of presumed denA mutants was judged qualitatively from the results of spot tests and quantitatively as efficiencies of plating of ten percent or less on plates with 40–60 mg HU in the top agar. The DNA-DNA hybridization test involved labelling *E. coli* DNA before phage infection and then 15 minutes after phage infection measuring the extent of host DNA degradation, determined by hybridization to *E. coli* filters. In addition, the extent of reutilization of degraded host DNA was determined by hybridization to T4 DNA filters.

The DNA-DNA hybridization tests were done as follows. The DNA in *E. coli* $B^E$ or CR63 cells grown in M9S media (infra) at 37° was labelled before phage infection with $(2-^{14}C)$ Uracil (1 μC/ml, 0.018 μmoles/ml, New England Nuclear). Aliquots of the labelled cells were subsequently infected with the phage being tested for the presence of the denA mutation or with different control phages (wild type, denA mutant, SaΔ9 mutant, and denA-SaΔ9). The infections were terminated 15 minutes after infection at 37° by adding five volumes of ice cold Tris/salt/EDTA (500 mM NaCl; 50 mM EDTA, pH 8.0; 10 mM tris-HCl, pH 8.0). Cell samples were collected by centrifugation, resuspended in 1.5 volumes of ice cold Tris/salt/EDTA, again pelleted and finally resuspended in 0.25 Volumes of Tris/salt/EDTA before being processed further or stored at −20° C. Duplicate one ml samples of uninfected cells were taken shortly before infection and single one ml samples were taken after infection.

Cells in 0.25 ml of Tris/Salt/EDTA were mixed with 0.25 ml of 1N NaOH. After five minutes in a boiling water bath, 0.55 ml of a neutralization mix was added (10 ml of 1N HCl; 8 ml of 20×SSC (SSC is 0.15M NaCl, 0.015M Sodium Citrate); 2 ml of 1M tris-HCl, pH 8.0 and 2 ml of water) and the pH was adjusted to 7.0±0.1. A 50 μl aliquot was set aside for acid precipitation and then 1.0 ml of formamide (O.D.$_{270}$ less than 0.15) was added. This procedure produces short fragments of single stranded DNA and completely hydrolyzes RNA, thus eliminating the possibility of labelled RNA hybridizing to the filters. After transferring these mixtures to glass scintillation vials, pencil marked nitrocellulose filters, prepared with different purified species of DNA, were wetted in 6×SSC and added to the vials. Hybridizations were done in a shaking water bath for 65–70 hours at 42° C. In each vial there were separate nitrocellulose filters for *E. coli* chromosomal DNA (8 μg of phenol extracted type VIII *E. coli* DNA purchased from Sigma), T4D wild type phage particle DNA (8 μg), and calf thymus (4 μg of phenol extracted type A calf thymus DNA purchased from Calbiochem). After hybridization the filters were batch washed, dried and counted in a toluene based scintillator. Although both hybridization criteria produce consistent results, the extent of hybridization to T4 filters is a more sensitive single criterion. Thus, a wild type denA gene in comparison to a mutant allele causes at least a five-fold increase in the extent of hybridization to T4 filters but decreases the extent of hybridization to *E. coli* DNA filters by only two to three-fold.

The alc TB1 mutation was detected in phage stocks by its ability to donate a marker allowing a gene 56 (amE51)-denA-denB triple mutant phage to plate on B834. Lysates of crosses made to combine this alc mutation with other mutations were plated on CR63 and "test" stocks were then made from a number of individual plaques. These test stocks were crossed to the 56amE51-denA-denB triple mutant and the progeny plated on B834. Individual progeny plaques from these crosses were tested for the presence of the gene 56am mutation on a lawn of S/6 containing gene 56 am mutant seed phage. If the gene 56 amber mutation was found in plaques from the B834 plates, the alc gene mutation must have been present in the test stock. B834 was frequently reisolated from single colonies as this strain accumulates amber suppressor mutations in our hands.

The presence of amber mutations in phage stocks was determined by standard spot tests.

The constructed bacteriophage strains are then employed as described below to produce the desired plasmid-phage recombinant genomes and phage-like particles containing these recombinants in accordance with this invention.

CHARACTERIZATION OF PHAGE PARTICLE DNA

Purified plasmid pBR322 and pVH691 DNAs were transformed as described above into C600, an *E. coli* strain permissive for amber mutatins. Strains of C600 carrying plasmids pVH691 and pBR322 will herein be called C600-pVH691 and C600-pBR322, respectively.

Populations of bacteriophage T4 phage particles were produced in C600-pVH691 that had been grown to approximately $2.10^8$/ml in M9S media (per liter: 7 g Na$_2$HPO$_4$, 3 g KH$_2$PO$_4$, 0.5 g NaCl, 1 g NH$_4$Cl, 0.001M MgSO$_4$, 0.0001M CaCl$_2$, 0.4% (w/v) glucose and 0.2% (w/v) casaminoacids-(Difco)). Aliquots of this culture were infected with stocks of several different T4 phage strains that had been prepared from single plaques of phage, by methods well known in the art, in CR63, a strain permissive for amber mutants, that had been grown in M9S media. The infections of C600-pVH691 were done at 37° C. with a multiplicity of infection (MOI) of between 5 and 20 viable phage particles. The particular phage strains used to produce these populations of phage particles, 23amA489, 23amA489-denA, 23amA489-SAΔ9, 23amA489-denA-alcTB1, 23amA489-denA-SaΔ9 and 23amA489-denA-SaΔ9-alcTB1 were constructed as described above. Numerous other mutations in each of these genes could be combined to produce strains having similar properties. The different populations of phage particles were produced by lysing the infected cultures of C600-pVH691 with chloroform between 30 and 60 minutes after infection. The lysed cultures (herein called lysates) were passed through millipore Millex-AA 0.8 μm filters and analyzed in several different ways for the presence of plasmid-phage recombinant genomes. This analysis will show that some populations of phage particles contain a small amount of an unusual type of plasmid-phage recombinant.

THE PREVIOUSLY KNOWN TYPE OF PLASMID-PHAGE RECOMBINATION

Figure 2:
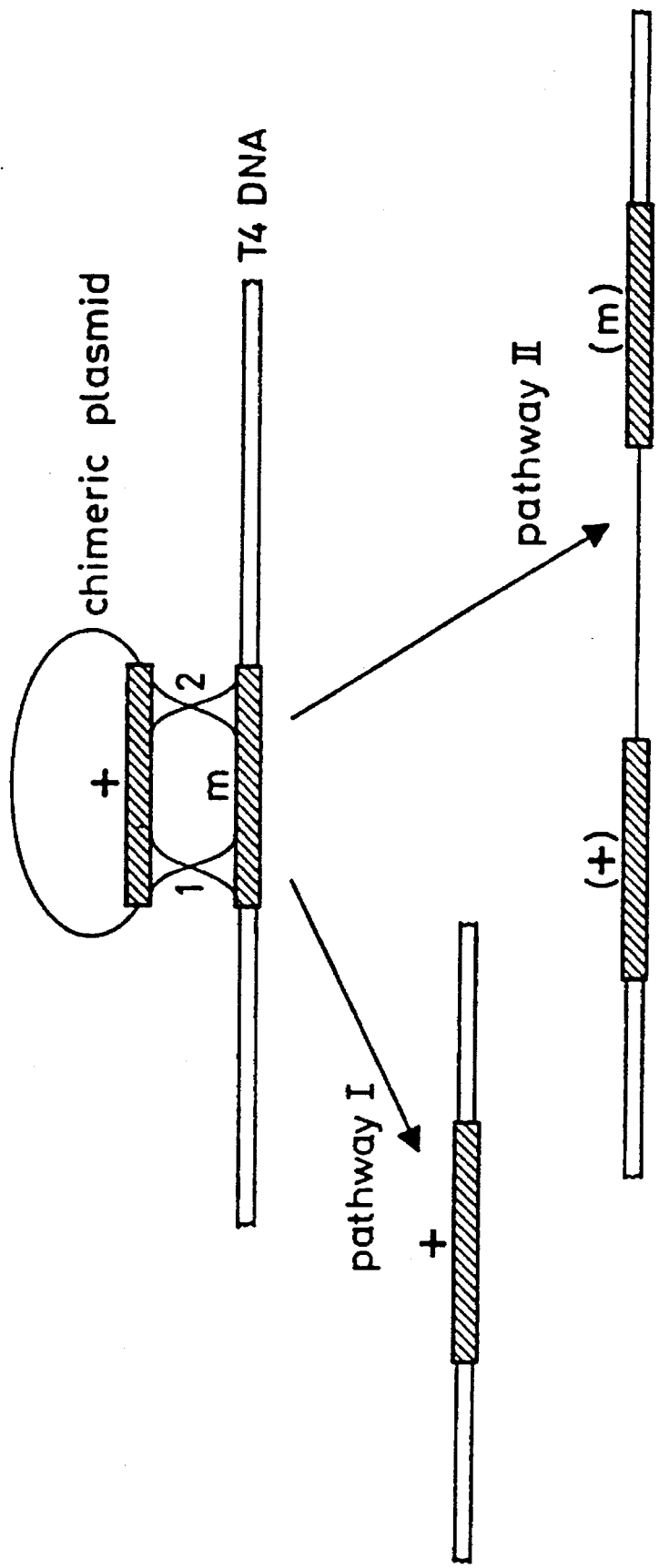
FIG. 2 is a schematic diagram of alternative path-ways for the formation of plasmid-phage recombinant genomes. In pathway (I), wild type T4 DNA(+) in the chimeric plasmid molecule can be substituted for homologous but mutant DNA(m) on a phage chromosome as a result of two crossovers, one to the left in region (1) and one to the right in region (2) of the mutant site. In pathway II, an entire chimeric plasmid molecule can be integrated into a phage genome as a result of a single crossover in either region (1) to the left or in region (2) to the right of the mutant site.

Marker rescue frequencies provide a measure of the efficiency with which a segment of cloned wild type T4 DNA is presumably substituted for a homologous, but mutant segment of DNA present in the infecting phage genomes. Thus, the level of marker rescue reflects the level of double genetic exchanges between cloned T4 DNA and homologous segments on infecting phage genomes. A formal representation of marker rescue recombination is given in FIG. 2, pathway I.

The results of marker rescue frequency measurements made with said lysates according to standard methods well known in the art are summarized in Table 1.

TABLE 1

| phage genotypes | gene 23 marker rescue frequencies |
| --- | --- |
| 23amA489 | 1.6% |
| 23amA489-denA | 0.45% |
| 23amA489-SaΔ9 | 1.7% |
| 23amA489-denA-alc | 0.49% |
| 23amA489-denA-SaΔ9 | 1.7% |

This analysis of viable phage particles does not reveal any significant differences between the phages tested. However, if methods of analysis are used that can detect genome in inviable phage particles then the results are strikingly different.

SOME PHAGE PARTICLES HAVE A SIGNIFICANT CAPACITY TO EXPRESS CLONED DNA

This analysis will show that there is a hidden potential in certain phage populations to express cloned DNA. As will become apparent, the nature of this potential is such that it can be exploited to develop T-even bacteriophages into potentially useful vectors for cloning and expressing large fragments of foreign DNA.

A second method for detecting cloned T4 DNA in progeny phage particles is as follows: The phase populations produced in C600-pVH691 are used to infect a bacterial strain that does not carry a suppressor for the amber mutation present in the phage genomes and the relative rates of synthesis of the mutant and wild type gene 23 polypeptides (gp23) are determined. This kind of analysis provides an indirect measure of the relative proportions of wild type and mutant copies of gene 23 DNA sequences.

Figure 3:
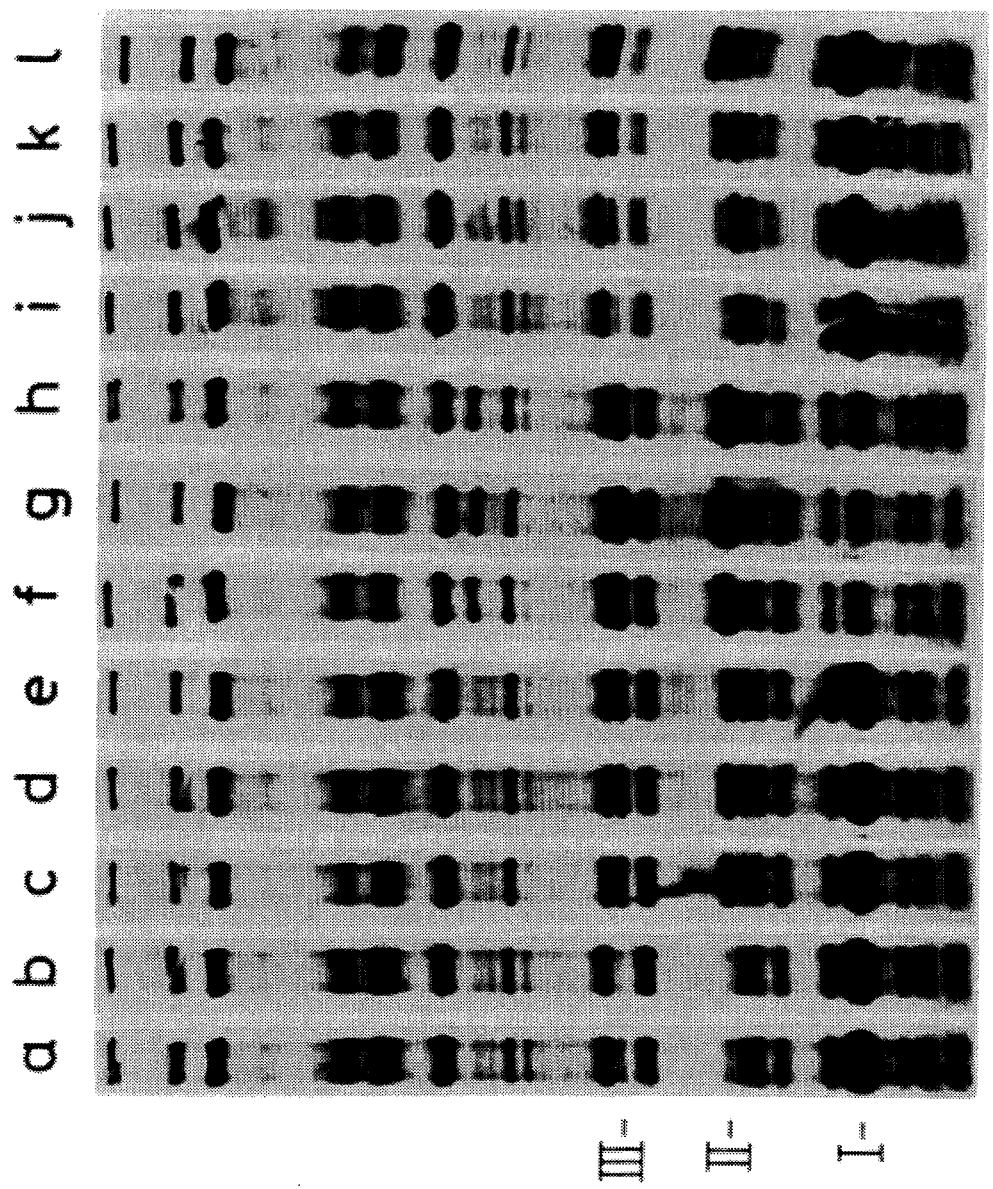
FIG. 3 displays an autoradiogram of the pattern of T4 proteins synthesized between 15 and 20 minutes after infection of an $E. coli$ strain non-permissive for amber mutants. The autoradiogram was prepared from a 10 percent SDS-polyacrylamide gel. The major polypeptide migrating at position (I) is derived from a mutant gene 23 DNA sequence and the polypetides migrating at positions (II) and (III) are derived from wild type gene 23 DNA sequences.

The data of FIG. 3 show that said populations of phage particles produced in C600-pVH691 differ significantly in the relative levels of functional copies of cloned wild type gene 23 DNA sequences. This autoradiogram shows the patterns of proteins synthesized between 15 and 20 minutes after infection of $B^E$-pBR322 at 37° C. Newly synthesized proteins were radioactively labelled with a mixture of $^{14}C$-labelled amino acids, the infected cells subsequently processed and electro-phoresized on a 10 percent SDS-polyacrylamide gel and an autoradiogram prepared essentially as described (infra) Columns (a–h) show the patterns obtained with said populations and columns (i–l) are the patterns obtained from reconstruction mixtures prepared by mixing appropriate volumes of mutant and wild type gene 23 stocks (23amA489-denA-SaΔ9 and denA-SaΔ9) (a) 23amA489, (b) 23amA489-denA, (c) 23amA489-SaΔ9, (d) 23amA489-denA-SaΔ9, (e) 23amA489-denA-SaΔ9-alcTB1, (f) T4D wild type, (g) SaΔ9, (h) denA-SaΔ9, (i) mixtures of 1 percent denA-SaΔ9 and 99 percent 23amA489-denA-SaΔ9, (j) mixtures of 3 percent denA-SaΔ9 and 97 percent 23amA489-denA-SaΔ9, (k) mixtures of 5 percent denA-SaΔ9 and 95 percent 23amA489-denA-SaΔ9, (l) mixtures of 10 percent denA-SaΔ9 and 90 percent 23amA489-denA-SaΔ9.

The amounts of wild type gp23 synthesized with the reconstruction mixtures containing one and three percent wild type gene 23 phage particles (columns (i) and (j)) are the levels predicted for said populations by the marker rescue data (Table 1). In fact, the marker rescue data and the wild type gp23 synthesis data are consistent with one another for said populations that do not carry the denB gene deletion. In contrast, the marker rescue data significantly underestimates the capacity of the denB mutant populations to synthesize wild type gp23.

It is apparent that the extra capacity to express cloned DNA sequences should not be limited to the expression of T4 genes, but could be applied through the use of molecular biology techniques, to the synthesis of an industrial gene product. However, in order to be able to manipulate the extra capacity of denB mutant populations to express cloned DNA sequences, it is necessary to identify the phage particles having this capacity. This was done by using a technique that can detect functional genes in inviable phage particles.

THE HIDDEN CAPACITY TO EXPRESS CLONED DNA RESIDUES IN A SMALL FRACTION OF INVIABLE PHAGE PARTICLES

The analysis done in this section enables us to conclude that in denB mutant progeny phage populations there are inviable particles containing cloned DNA and that the level of these inviable particles is low. The method of analysis used is a genetic complementation test for the wild type gene 23 sequences present in the cloned DNA. The significance of these findings for developing T-even bacteriophages into cloning and expression vectors is that one will have to develop special methods for propagating these inviable particles.

THE CONTRIBUTOR TEST

A culture of $B^E$ (a strain that is nonpermissive for amber mutations) was grown at 37° C. to approximately $2.10^8$/ml in H-broth (per liter: 8 g nutrient broth (Difco), 5 g NaCl, 5 g Bacto peptone, 1 g glucose and 3 ml of 0.5N NaOH) ), centrifuged and resuspended at approximately $4.10^8$/ml in the same medium. Each of the populations of phage particles to be tested for the titre of complementation activity (herein called the test stocks) was diluted in H-broth in such a way as to contain approximately $6°10^6$ viable, wild type gene 23 particles. A helper phage stock (23amA489-denA-SaΔ9) was diluted in H-broth in such a way as to produce a titre of approximately $1°10^9$ total viable phage particles (as measured by plating on CR63, a strain permissive for amber mutations). 20 μl of each test stock was then added to 2.0 ml of H-broth and another 20 μl added to 2.0 ml of the helper phage stock (at $1.10^9$/ml). In addition, one tube containing 2.0 ml of only the helper phage stock was prepared and another tube containing 2.0 ml of only the control phage stock (denA-SaΔ9 at approximately $1.0^9$/ml) were prepared. All of these phage stocks and mixtures of phage stocks will be called the input phage.

The complementation test for detecting inviable contributors was done at room temperature by mixing 0.5 ml of bacteria ($B^E$) and 0.5 ml of each phage preparation (each test stock alone, each test stock mixed with the helper phage, the helper phage stock alone and the control phage stock). Eight minutes after mixing the bacteria and phage, 0.2 ml of T4 specific antisera was added. After an additional eight minutes, that is, 16 minutes after infection, the cultures were diluted various amounts and plated on CR63. This plating on CR63 measures the infective centers, that is, the number of infected $B^E$ cells that are able to produce at least one viable progeny phage be it either amber gene 23 mutant or wild type for gene 23. At 17 minutes after infection chloroform was added to each infected culture in order to kill the infected bacteria before any progeny phage were produced and an aliquot of each of these chloroformed cultures was plated on CR63. This plating on CR63 provides a measure of the number of input phage that did not absorb to the $B^E$ bacteria. In addition to plating on CR63 for measurements of infective centers and unadsorbed phage particles, all of the input phage stocks and mixtures were assayed on CR63 for total viable phage and on S/6 (a non-permissive strain for amber mutations) for viable wild type gene 23 phage.

The data given in Table 2 have been corrected for the level of unadsorbed phage in each infection. The efficiency of detection of the control phage (denA-SaΔ9) in this complementation test was 91 percent. The data given in columns 1 and 2 of Table 2 are the levels of infective centers observed without and with the helper phage, respectively. The values given in column 3 of Table 2 was obtained by dividing the values in column 2 by the values in column 1.

TABLE 2

COMPLEMENTATION TITRES

| phage genotype | WITHOUT HELPER | WITH HELPER | RATIO |
|---|---|---|---|
| 23amA489 | $4.8 \times 10^4$ | $5.5 \times 10^4$ | 1.1 |
| 23amA489-denA | $4.7 \times 10^4$ | $5.4 \times 10^4$ | 1.1 |
| 23amA489-SaΔ9 | $8.7 \times 10^4$ | $2.2 \times 10^5$ | 2.5 |
| 23amA489-denA-alc | $5.4 \times 10^4$ | $4.8 \times 10^4$ | 0.89 |
| 23amA489-denA-SΔ9 | $9.3 \times 10^4$ | $3.6 \times 10^5$ | 3.9 |

The results of the contributor test clearly show that inviable phage particles containing cloned wild type T4 DNA are present in significant amounts in this experiment when said phages carry the denB gene deletion SaΔ9. We call these dead phage particles, "inviable contributors". Thus, the inviable contributors are more abundant than marker rescue recombinants in the denB mutant populations.

MOLECULAR STRUCTURE OF THE INVIABLE PHAGE GENOMES

In order to be able to adapt the inviable particles containing cloned DNA to the production of desired non-T-even gene products it is necessary to establish the structure of the DNA in these particles. The structure of this DNA was probed through the use of restriction endonucleases. However, normal T4 DNA contains the unusual base hydroxymethylcytosine and consequently is resistant to most restriction endonucleases. Thus, for this analysis we have used abnormal T4 DNA that contains cytosine, the base normally present in most other chromosomes.

The results of this analysis show that it is possible to clone large fragments of foreign DNA into phage chromosomes and that in doing so one can make individual molecules composed of multicopy sequences of the cloned DNA and only single copy sequences of the phage vector DNA.

These practical considerations follow from the following characteristics of the recombinants: (1) complete chimeric plasmid molecules can become integrated into phage genomes in the region of shared homology and (2) multiple copies of complete plasmid molecules can become integrated in tandem arrays. Plasmid-phage recombinant genomes having these characteristics are totally unknown in the prior art.

Cytosine-containing T4 DNA can be synthesized and then packaged into mature phage particles if $E.$ $coli$ $B^E$ cells are infected with phage that carry amber mutations in genes 42 and 56, point mutations in the denA and alc genes and a deletion covering the denB gene. Many other generally available mutations in each of these genes could equally well be employed to produce cytosine-containing T4 DNA.

PREPARATION OF CYTOSINE-CONTAINING DNA FROM T4 PHAGE PARTICLES PRODUCED IN E. COLI STRAINS $B^E$-pBR322 AND $B^E$-pVH737

200 ml cultures of E. coli $B^E$-pBR322 and $B^E$-pVH737 were grown at 37° C. in M9S media to approximately $2.10^8$/ml and then infected at multiplicities of between 5 and 10 with a quintuple mutant phage (56amE51-42amN55-denA-SaΔ9-alcTB1) and incubated for 120 minutes when the culture was lysed with chloroform. The viable phage titres were between 3.5 and $8.10^9$/ml on the permissive host B834. After a low speed centrifugation, progeny phage were pelleted by centrifugation at approximately 10000 g for 4 hours, resuspended in 2 ml of a phosphate buffer (per liter: 4 g NaCl, 3 g $KH_2PO_4$, and 7 g $Na_2HPO_4$) and then further purified on 30 ml neutral 5 to 20 percent sucrose gradients containing 200 mM NaCl and 10 mM tris-HCl, pH 8.0 to separate mature phage particles from free DNA in the cell lysates. These gradients were centrifuged for 45 minutes at 15000 rpm and 20° C. in an SW27 rotor. The visible bands of phage particles were removed from the gradients, dialysized against Tris/EDTA, extracted twice at room temperature with phenol (pH 8.0): chloroform (1:1) and then the DNA was ethanol precipitated. Dried pellets of DNA were resuspended in 1.0 ml of Tris/EDTA. This cytosine containing DNA was then analysed as described below, by Southern blots.

Duplicate Southern blots were separately hybridized for 18 hours at 42° C. in 20 ml of 50% Formadide-2×SSC containing 15 μg/ml of sonicated, heat denatured calf thymus DNA and approximately 2–3μg of nicktranslated probe DNA. After hybridization the blots were washed, dried and then exposed to X-ray film (X-Omat from Kodak). Developed films were traced with a Joyce-Loebel recording microdensitometer and areas under peaks were measured with a electronic graphic calculator from Neumonics Corp.

A MODEL FOR THE MOLECULAR STRUCTURE OF PLASMID-PHAGE RECOMBINANT GENOMES

As an aid to the interpretation of data and to understanding the potential utility of these recombinants for cloning and expressing foreign DNA sequences we first present a model for the structure of one such recombinant and then confirm the model.

Figure 4A:
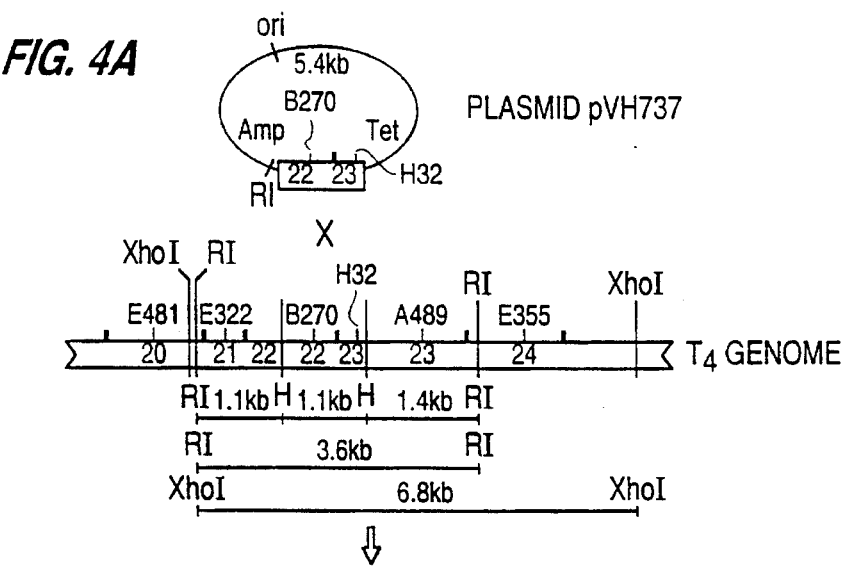
FIGS. 4A–4D are a schematic drawing of plasmid pVH737 and the molecular structure of the plasmid-phage recombinant genomes that can be constructed from pVH737 by the kind of recombination shown in FIG. 2, pathway (II). EcoR1 and HindIII recognition sites are indicated by (R1) and (H), respectively. Divisions between T4 genes are indicated by the solid bars above the horizontal bars that indicate T4 DNA. The sites of T4 amber mutations within EcoR1, HindIII and EcoR1-HindIII restriction fragments are shown. The drawings are not to scale.

A cloned T4 HindIII restriction fragment was used to establish the structure of the plasmid-phage recombinant genomes. Reciprocal, Campbell-type recombination between homologous segments of T4 DNA leads to the integration of a complete plasmid molecule into a phage genome FIG. 4(a) and (b)). Additional recombinational events can lead to the formation of dimer (FIG. 4(c)) and higher order inserts (see below). Digestion of these structures with restriction endonuclease EcoRI leads to the formation of restriction fragments having a number of unique properties.

Figure 4B:
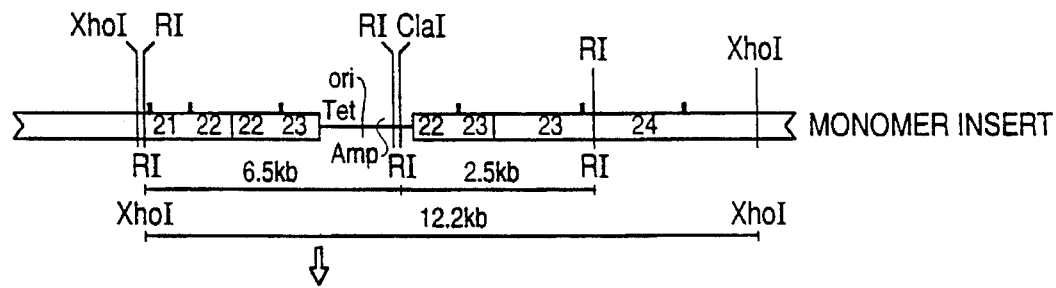

If dimer and higher order inserts of pVH737 occur, gene 22 and gene 23 DNA will be in EcoRI restriction fragments of approximately 2.5, 3.6, 5.4 and 6.5 kb. Plasmid pBR322 DNA should be in EcoRI restriction fragments of identical sizes except that it should be absent from the one (3.6 kb) corresponding to the gene 21–23 region of a normal phage genome. The molar ratios of these different sized restriction fragments will depend, in part, on the relative proportions of monomer and higher order inserts in the population of DNA molecules. However, for every phage genome containing at least one complete plasmid molecule there should be equimolar amounts of the 2.5 and the 6.5 kb fragments (FIG. 4(b) and (c)).

The 6.5 kb EcoRI restriction fragment is of particular interest. This restriction fragment should contain T4 DNA that was not present in the starting plasmid as well as pBR322 DNA and the original cloned DNA. Considering the orientation of the DNA cloned in plasmid pVH737 (see FIG. 4(a)), one can predict that the additional T4 DNA present in the 6.5 kb fragment should be gene 21 and gene 22 DNA, but not the C-terminal coding portion of gene 23.

In addition, this 6.5 kb fragment might be able to form an autonomous plasmid molecule that can be selectively isolated. That is, this fragment contains an intact pBR322 origin of replication and an intact drug resistance determinant.

SOUTHERN BLOT ANALYSIS OF PLASMID-PHAGE RECOMBINANT GENOMES

The results of this physical analysis of phage particle DNA confirms several predictions of the described model. More important for the purpose of adapting this type of recombinant molecule to serve as a general cloning or expression vehicle, this knowledge sets definite practical guidelines for approaching this task.

Figure 5:
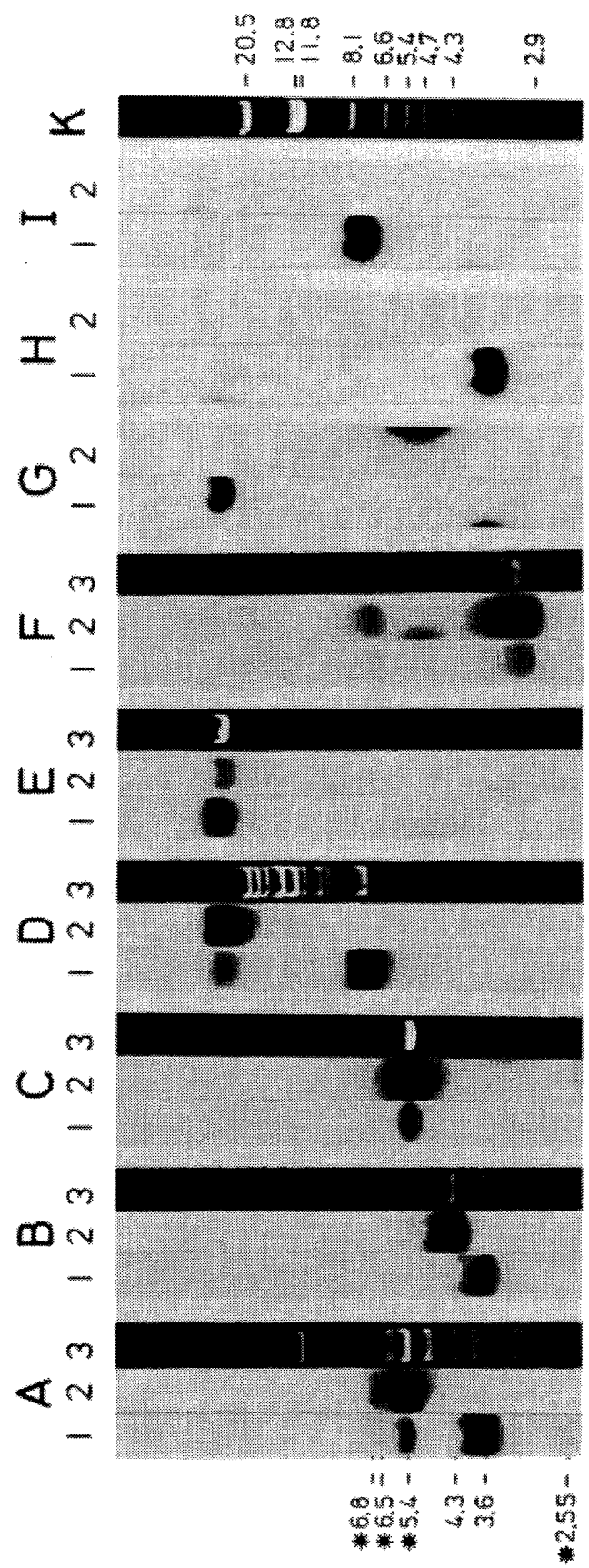
FIG. 5 displays the results of a Southern blot analysis of DNA isolated from mature T4 phage particles.

This physical evidence is presented in FIG. 5. Undigested and restriction endonuclease digested DNA was first subjected to electrophoresis on an 0.75 percent agarose gel (Sigma Type II, gel and running buffer were 40 mM tris-acetate, pH 8.0; 20 mM sodium acetate, 0.1 mM EDTA) and then transferred bidirectionally to duplicate nitrocellulose sheet (Schleider and Schull, type BA85) Approximately 0.2 μg of phage particle DNA, 0.05 μg of the different pBR322 derivatives and approximately 1 μg of R100 plasmid DNA were loaded onto the slots of this agarose gel.

The positions of DNA species containing pBR322 or T4 gene 21–23 DNA were identified by DNA-DNA hybridization of the duplicate blots with nick translated probes. Plasmid pBR322 DNA and purified gene 21–23 EcoR1 restriction fragments (approximately 2–3 μg of each) were nick translated with ($\alpha$-$^{32}$P) dATP (approximately 3000 Ci/mole from Amersham). The nick translations were terminated by adding three ml of 50 percent formaide- 2×SSC, then placed in a boiling water bath for 10 minutes, cooled to room temperature and used immediately for hybridizations. The purified gene 21–23 restriction fragment was prepared by digesting plasmid pVH691 DNA with EcoRl, separating the T4 DNA from the pBR322 vector DNA by electrophoresis in a 0.8 percent agarose slab gel and then extracting the T4 DNA from a slice of the agarose gel. The pBR322 plasmid vector DNA was purified on a cesium chloride-ethidium bromide gradient from a cleared lysate.

The identity of the DNA samples shown in FIG. 5 and the nick translated probes used to identify the location of particular species of DNA in each sample are as follows:

(A) EcoRI digest of phage particle DNA produced in B$^E$.pVH737; (B) EcoRI digest of plasmid pVH691 DNA;(C) EcoRI
digest of plasmid pVH737; (D) XhoI digest of phage particle DNA produced in B$^E$.pVH737; (E) uncut phage particle DNA produced in B$^E$.pVH737; (F) uncut plasmid pVH737 DNA; (G) uncut phage particle DNA produced in B$^E$.pBR322; (H) EcoRI digest of particle DNA produced in B$^E$.pBR322; (K) Size markers provided by an EcoRI digest of plasmid R100 DNA. (1) probed with T4 gene 21–23 DNA; (2) probed with pBR322 DNA; (3) Restriction fragment pattern observed on the 0.75 percent agarose gel used for making the DNA blots. Sizes, in kilobases (kb), of R100 restriction fragments are indicated on the right hand margin. The sizes indicated on the left margin, which identify T4 and pBR322 DNA containing fragments, are derived from published sources, and from the values (marked*) given in FIGS. 4A–4D. These latter sizes correspond closely, to within 10 percent, to the sizes calculated for these restriction fragment from their relative positions in the agarose gel and on the autoradiograms.

Standard analysis of the results obtained with EcoRI and XhoI digested DNA conform to all of the predictions made above concerning the number and size of restriction fragments, the molar ratio of fragments and the probable genetic composition of the fragments.

Of particular interest are the comparisons indicating that multiple copies of complete plasmid molecules can be inserted into phage chromosomes. This can be seen by comparing the relative intensities of the bands corresponding to the 6.5 kb and 5.4 kb EcoRI restriction fragments in FIG. 5 (columns A1, A2). The molar ratio of these two bands, as determined from microdensitometer tracings, is at least eight. Thus, the average number of inserts may be as great as nine to ten. Genetic evidence consistent with multiple inserts is given below.

Since the 5.4 kb EcoRI band corresponds in size to the EcoRI digest product of the starting plasmid pVH737 (FIG. 5, column C1), it seems necessary to conclude that the multiple inserts occur in tandem arrays.

Control experiments show that detectable amounts of pBR322 DNA do not integrate into the gene 21–23 region of phage genomes unless a gene 21–23 restriction fragment is present in the vector. This can be seen from the results of the hybridizations done with either the gene 21–23 or the pBR322 probe using XhoI cut DNA derived from cells containing the plasmid vector alone (FIG. 5, columns I1 and I2). That is, neither probe detects a band of 11 kb in XhoI digests corresponding to a monomer insert and the gene 21–23 probe detects only bands corresponding in size to those expected in digests of normal phage genomes.

The data presented in FIG. 5 show that the presence of cloned T4 DNA in pBR322 significantly increases the amount of pBR322 DNA that can be packaged into phage particles (FIG. 5, compare column A2 with columns G2, H2 and I2).

Thus, T4 insert-dependent packaging of pBR322 DNA into phage particles is much more efficient than the T4 insert-dependent packaging.

The Southern blot data is consistent with the contributor data (supra) in indicating that less than ten percent of the total population of phage particle genomes contain the unusual recombinants: compare the densities of the bands corresponding to the boundary copy and the gene 21–23 EcoRI restriction fragment derived from normal T4 genomes (FIG. 5, column A1).

A GENOME WALK

The cytosine-containing DNA isolated from T4 phage particles produced in B$^E$ VH737, described above was also used to illustrate a genome walk. This demonstration confirms additional predictions about the structure of the unusual genomes.

Integration of entire plasmid molecules into specific and predictable regions of the T4 genomes can be demonstrated by using integrated plasmid molecules to clone adjacent regions of the T4 genome. In a phage genome containing integrated plasmid molecules, the pBR322 DNA will be covalently linked to T4 sequences that were not present in the original cloned restriction fragment. However, if a phage genome contains multiple plasmid inserts, it will be the boundary copies of the integrated plasmid molecules but not the internal copies that can be used to clone the adjacent T4 DNA sequences. The cloning of adjacent segments of T4 DNA by use of the integrated plasmid molecules is herein called a genome walk.

Boundary copies of integrated plasmid molecules can be distinguished from internal copies after digestion of the phage genomes with a restriction endonuclease having one recognition site in the original chimeric plasmid and additional recognition sites in the adjacent region of the T4 genome. Thus, for the structures in FIGS. 4A–4D, the restriction endonuclease EcoRI can be used to biologically distinguish between internal copies and the left-hand boundary copies. EcoRI restriction fragments containing internal copies should be physically and genetically indistinguishable from the starting plasmid used in this experiment. In particular, EcoRI restriction fragments containing the left-hand boundary copies should be larger and they should contain adjacent DNA not present in the internal copies (see FIGS. 4A–4D).

EcoRI restriction fragments containing internal copies and the left-hand boundary copies are similar in that both should contain intact pBR322 origin of replication and an intact ampicillin drug resistance determinant. Note that the 2.5 kb EcoRI restriction fragment containing the right-hand boundary copy is missing both the pBR322 origin of replication and a drug resistance determinant. Thus, it should be possible to isolate plasmids containing either internal or left-hand boundary copies, but not right-hand boundary copies after ligation of the EcoRI restriction fragments and transformation into bacterial cells. In addition, it should be possible to genetically determine whether any particular plasmid isolated in this way was derived from an internal or a boundary copy of the integrated plasmid molecules.

PRODUCTION AND IDENTIFICATION OF AUTONOMOUS PLASMID MOLECULES THAT ILLUSTRATE A GENOME WALK

All restrictions endonuclease digestions were done in the TA buffer (supra). The preparation of DNA used to illustrate the genome walk was the same as that used for making the Southern blots described above. DNA isolated from phage particles produced in $B^E$-pVH737 was digested with EcoRI and ligated with T4 DNA ligase under standard conditions, transformed into C600 as described above and spread on LA plates containing 10 µg/ml ampicillin as described above. Marker rescue tests were done to genetically test for the presence of various segments of cloned T4 DNA. The original cloned HindIII restriction fragment was detected with amH32(g23). The two adjacent T4 HindIII-EcoRI restriction fragments were detected with amA489(g23) and amE322(g21). The relative positions of restriction fragments in this region of the T4 chromosome and the T4 markers used to genetically identify each is shown in FIGS. 4A–4D.

The results presented in Table 3 show that ampicillin colonies can be recovered after restriction endonuclease digestion, ligation and transformation of DNA isolated from mature T4 phage particles produced in $B^E$-pVH737.

In addition, all of the colonies derived from the phage particle DNA produced in bacteria carrying the plasmid pVH737 can rescue a T4 gene 23 marker (amH32) present in the original cloned HindIII fragment.

Figure 4C:
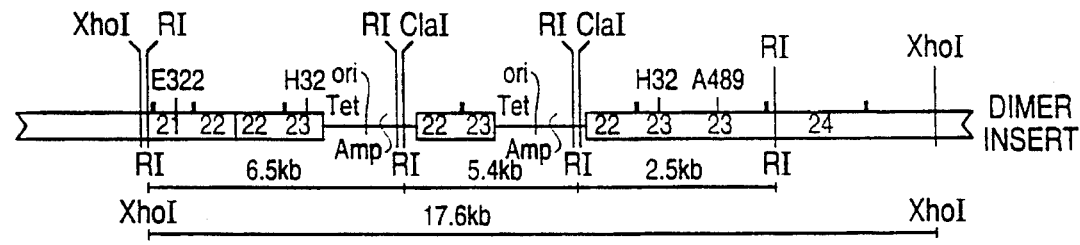
Figure 4D:
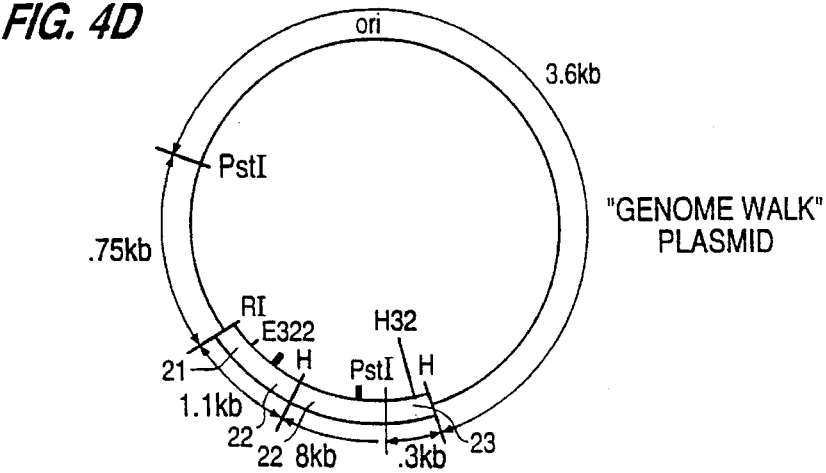

Nearly ten percent of the colonies tested contain the additional T4 marker (amE322) predicted to be present in the left-hand boundary copies (Table 3, line 2; see also FIG. 4(c)). In contrast, none of the colonies tested were able to rescue the gene 23 marker (amA489) that would indicate that the right-hand boundary copies have been recovered in this experiment. An additional three percent of the colonies tested contain T4 DNA that is not immediately adjacent to the original cloned HindIII restriction fragment (Table 3, lines 3 and 4). Analysis of plasmid DNA isolated from cells giving positive marker rescue tests for either gene 20 or gene 24 DNA suggests that these plasmid molecules were formed during the ligation step by the insertion of additional EcoRI restriction fragments into 737-like plasmid molecules (data not shown). These colonies were not examined further.

MOLECULAR STRUCTURE OF AUTONOMOUS PLASMID MOLECULES THAT ILLUSTRATE A GENOME WALK

Figure 6:
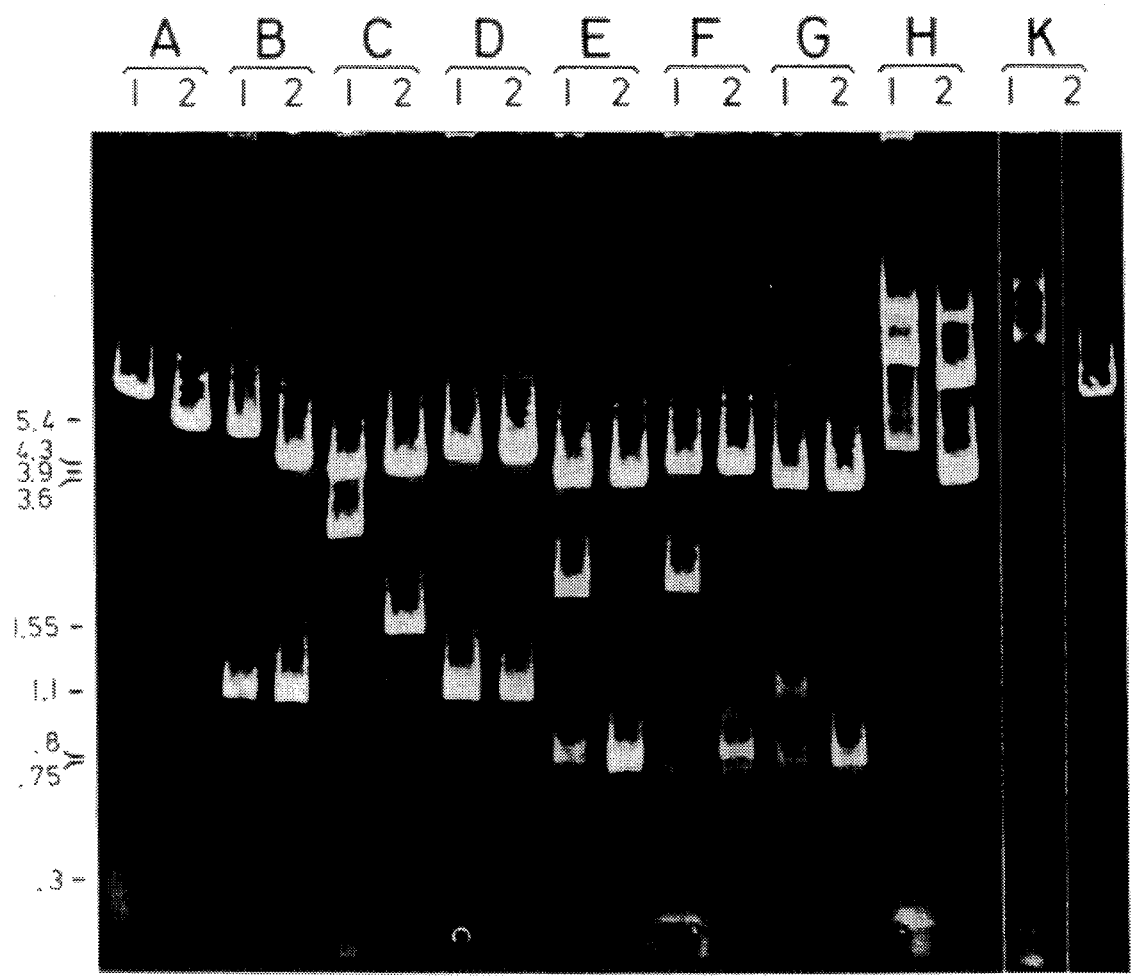
FIG. 6 displays the pattern of restriction fragments observed on a one percent agarose gel after electro-phoresis of restriction endonuclease digests. Plasmid pVH737 DNA is compared with DNA from a plasmid that illustrates a genome walk.

The molecular structure of autonomous plasmid molecules containing genetic markers expected only in the left-hand boundary copies conforms to the structure predicted in FIGS. 4A–4D. This was shown by comparing restriction endonuclease digest patterns obtained with plasmid DNA isolated from several of these colonies with the patterns obtained after digestion of purified plasmid pVH737 DNA (FIG. 6).

Mini-preps of plasmid DNAs amplified with 200 µg/ml chloramphenicol from selected colonies were prepared after single colony purification. These plasmid DNA's were digested with various restriction endonucleases and electrophoresized in one percent agarose slab gels as described above. The absence of ClaI restriction sites in either the T4 gene 22–23 HindIII restriction fragment or the gene 21–22 EcoRI-HindIII restriction fragment was determined from the ClaI digest patterns (see columns K1 and K2). The sizes given on the left margin are the sizes of pVH737 restriction fragments. Additional sizes can be determined by extrapolation from the values given.

(1) DNA from the plasmid product of the genome walk; (2) DNA from the plasmid pVH737; (A) EcoRI digested; (B) HindIII digested; (C) PstI digested; (D) EcoRI plus HindIII digested; (E) HindIII plus PstI digested; (F) EcoRI plus PstI digested; (G) PstI plus EcoRI plus HindIII digested; (H) uncut samples; (K) ClaI digested samples.

Standard analysis of these restriction digest patterns shows that the number and sizes of the restriction fragments

TABLE 3

Summary of marker rescue tests

| Plasmed type | Gene 20 | Gene 21 | Gene 23 (amH32) | Gene 23 (amA489) | Gene 24 | Colonies tested |
|---|---|---|---|---|---|---|
| 1. Parental type | 0 | 0 | + | 0 | 0 | 261(87.2%) |
| 2. Genome walkers | 0 | + | + | 0 | 0 | 29(9.8%) |
| 3. Parental type containing an additional EcoRI fragment | + | 0 | + | 0 | 0 | 2(0.7%) |
| 4. Parental type containing an additional EcoRI fragment | 0 | 0 | + | 0 | + | 7(2.3%) |
| | | | | | TOTAL | 299(100%) | detected after single and multiple enzyme digestions conform to what one can predict from the structures shown in FIGS. 4A–4D, In addition this analysis allows the conclusions that the orientation of the cloned HindIII restriction fragment in this new plasmid is the same as in the original pVH737 plasmid, that the additional T4 DNA present in the plasmid has been inserted at the predicted site and that the small EcoRI-HindIII restriction fragment of the pBR322 plasmid vector is probably deleted, as predicted from the structures shown in FIGS. 4A–4D.

The genome walk experiment illustrates a useful technique not available to other methods for cloning into T-even genomes. After a DNA fragment has been cloned, it is often desirable to be able to retrieve a copy of the cloned DNA for examination. Since entire plasmid molecules are integrated into phage genomes, one can retrieve an autonomously replicating plasmid molecule containing a copy of the cloned DNA by the the method illustrated.

Thus far we have described the nature of recombinant DNA molecules produced according to this invention. These recombinants are composed of tandemly repeated copies of entire plasmid molecules covalently attached to single copies of normal phage genes. This property is useful because it means that the relative gene dosage of the pre-determined non-T-even DNA sequence can be very high. We have also shown that phage particles containing these recombinants are inviable. This information is important because it means that special procedures need to be adopted to increase the supply of such phage-like particles. Finally, we have shown that initially only a small fraction of the total phage particles are of this type.

The yield of these novel recombinant molecules appears to be very low, only a few percent of the total phage particle genomes. The usefulness of these recombinants would obviously be increased if one could increase the yield of them. The ideal way to do this would be to to be able to treat them like normal phage chromosomes. That is, since these recombinant genomes can be packaged into phage-like particles and subsequently introduced into other bacteria, one might think that pure clones of individual recombinants could be identified and propagated by standard microbiological procedures. However, individual phage-like particles containing these recombinants, unlike normal phage particles, cannot be clonally reproduced because each of these particles lacks a significant and essential fraction of the phage genome. In addition, each of the phase-like particles produced in an individual cell is genetically different because each will be missing a different segment of the phage genome.

We have developed a simple process to increase the yield of these recombinants by modifying the normal process used for making a phage stock. Although we can significantly increase the yield of these novel recombinants we do not produce a pure culture containing only the phage-like particles. Nevertheless, the phage-like particles produced can be handled substantially by the standard methods used for normal phage stocks.

Our process for increasing the yield of said recombinants utilizes a cloned T4 restriction fragment that has been characterized as a T4 origin of replication. We first present the characterization of this T4 restriction fragment and then illustrate its use for increasing the yield of said recombinant molecules.

CHARACTERIZATION OF A T4 RESTRICTION FRAGMENT USEFUL IN THE REITERATED PROCESS AS A T4 ORIGIN OF REPLICATION

Figure 7:
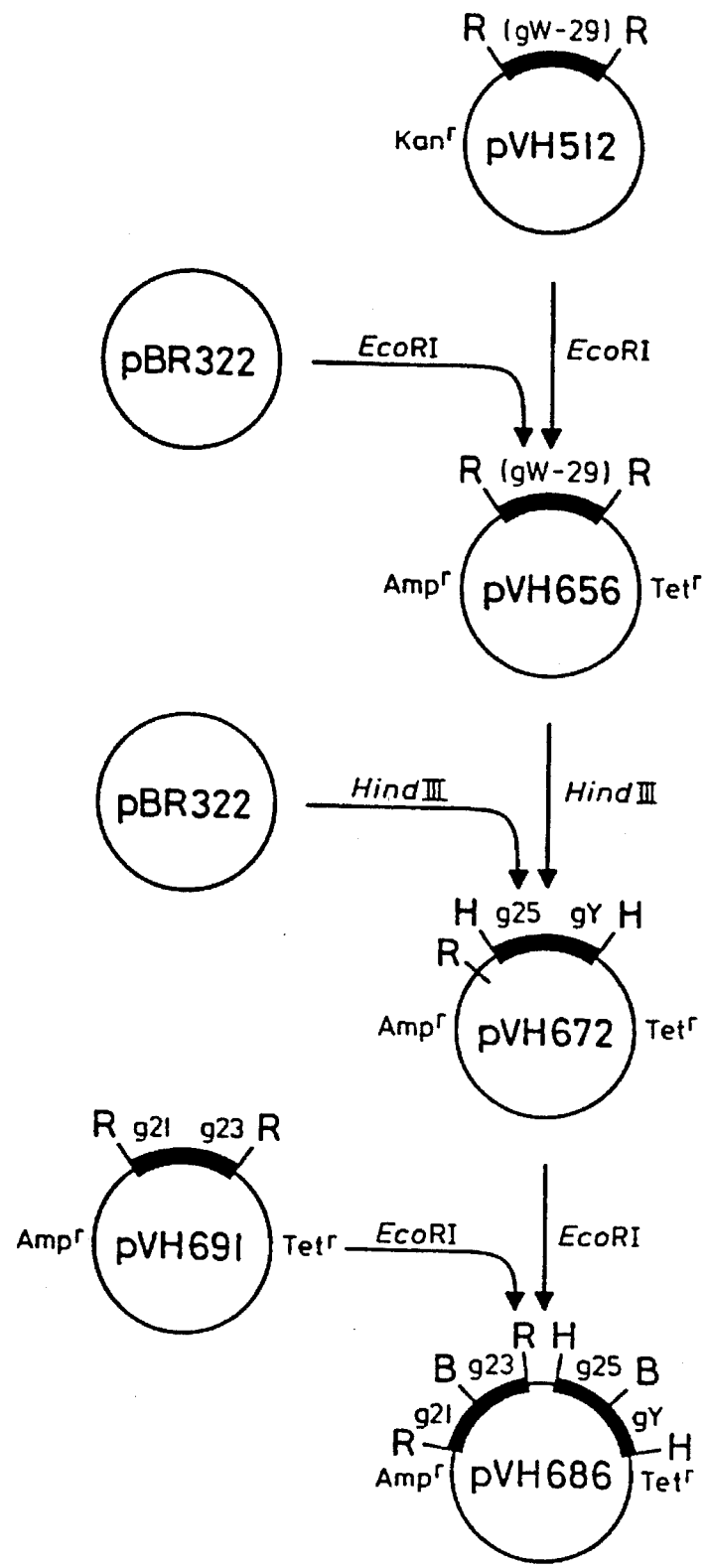
FIG. 7 summarizes the derivation of the recombinant DNA plasmid pVH686. The relative positions of the sites recognized by EcoRI, HindIII and BglII are indicated by (R), (H) and (B), respectively. T4 DNA is represented by the darkened blocks and the vector DNA, which is pBR322 in all of these plasmid except pVH512, in which case it is pCR1, is represented by a line. T4 genes are indicated by a small case (g) follows by a large case letter or a number. A parenthesis around the T4 genes indicates that the orientation of the T4 insert is unknown.

This cloned T4 restriction fragment is useful because it allows us to use (and to monitor the progress of) the reiterated enrichment process (infra) for a number of cycles under conditions where the level of production of viable marker rescue recombinants remains lower than the level of production of the inviable recombinants of this invention. 10 The recombinant DNA molecule used to characterize this cloned T4 restriction fragment and to illustrate the process used to increase the yield of the inviable phage-like particles of this invention is a derivative of the plasmid vector pBR322 and is herein called plasmid pVH686. Plasmid pVH686 was constructed by methods similar to those described above for plasmids pVH691 and pVH737. An outline of the derivation is shown in FIG. 7.

Plasmid pVH686 was derived from plasmids pVH672 and pVH652 as described below. Plasmid pVH672 was derived from pVH656 (a pBR322 derivative of pVH512 containing T4 genes w-29 on an EcoRI restriction fragment, Young et al., op cit) by digestion of plasmid pVH656 and pBR322 DNAs with HindIII and ligating them together in vitro with T4 DNA ligase and transforming into competent C600 cells. Clones containing a gene y marker (Y100) and two gene 25 markers (amB266 and amB287), but not any markers from genes 26 to 29, were identified by marker rescue tests as described above.

Clones containing both possible orientations of the T4 gene 25-y HindIII restriction fragment were identified by the standard technique of digesting purified plasmid DNA with an appropriate restriction endonuclease (in this case PstI) and analysing the digest product patterns after electrophoresis into agarose gels. Thus, plasmids pVH672 (having the orientation indicated in FIG. 7) and pVH671 (having the opposite orientation) were isolated. Plasmid pVH672 DNA was used in the construction of plasmid pVH686 and plasmid pVH671 DNA was used to construct plasmid pVH685 (infra).

Plasmid pVH672 is a dimer containing a T4 HindIII restriction fragment of approximately 1400 base pairs. Plasmid pVH686 was derived from pVH672 by digesting pVH672 and pVH652 DNAs with EcoRI and ligating them together (ca. 0.4 μg each) in vitro with T4 DNA ligase. Plasmid pVH672 contains an EcoRI site in the vector portion of the chimeric plasmid molecule but does not contain any EcoRI sites within the cloned T4 HindIII restriction fragment. After transformation of the ligation mixture containing EcoRI-cut plasmids pVH652 and pVH672 into C600 as described above, a clone containing gene 21–23 markers and gene 25 marker was identified by marker rescue tests as described above. The orientations of both of the cloned T4 restriction fragments can be established by a simple genetic test, which was done as follows. Purified plasmid pVH686 DNA was prepared from cleared lysates as described above, digested with BglII, recirculated in vitro with T4 DNA ligase and transformed into C600 as described above. Many of the transformants had lost gene 22, gene 23 and gene 25 markers while retaining the y gene marker, the gene 21 markers and the C-terminal coding portion of gene 22. Thus the orientation of the two separate T4 restriction fragments in pVH686 must be as shown in FIG. 7. This genetic analysis was confirmed by digesting purified plasmid DNA with PstI followed by analysis of restriction digest patterns on agarose gels.

An identical procedure was followed to construct and to establish the orientations of three other plasmids containing these two T4 restriction fragments. (Since each fragment can be cloned in either of two orientations, a total of four different plasmids containing these two fragments can be constructed.) Any of these four plasmids could be used to characterize the cloned T4 origin of replication and to illustrate the reiterated process (infra).

The produced recombinant DNA molecule, pVH686 was then treated as described below to characterize a cloned T4 origin of replication and to illustrate the reiterated process used to increase the yield of the inviable phage-like particles of this invention.

Figure 8:
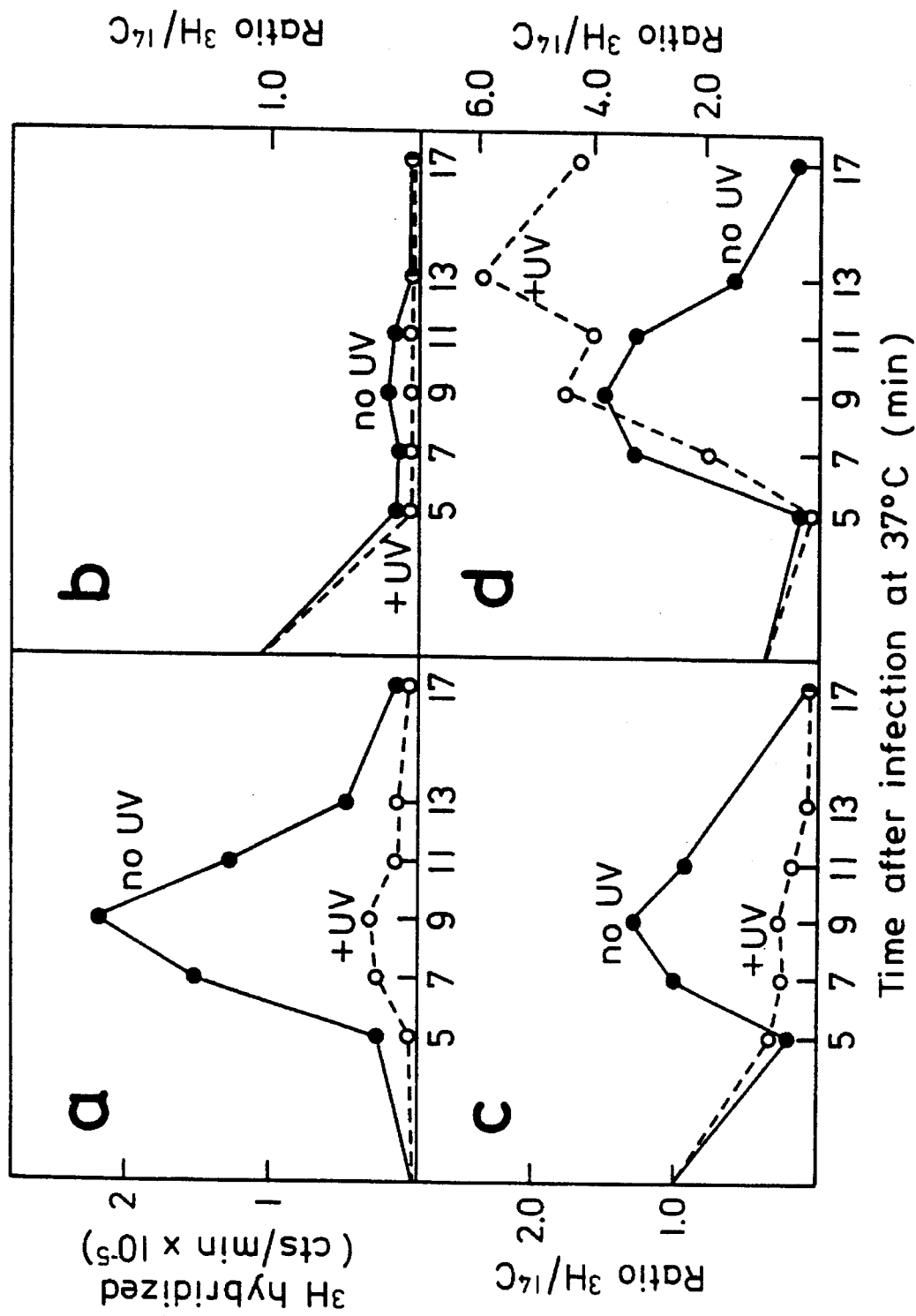
FIG. 8 presents a DNA-DNA hybridization analysis of the effects of cloned T4 restriction fragments on the synthesis of pBR322 DNA in cells infected with T4 phage particles that have or have not been treated with ultraviolet irradiation. (a) T4 DNA in $B^E$-pVH686 (b) pBR322 DNA in $B^E$-pBR322 (c) pBR322 DNA in $B^E$-pVH691 (d) pBR322 DNA in $B^E$-pVH686.

Autonomous replication of the plasmid vector pBR322 is blocked in cells infected with the T-even phage T4. If pBR322 contains a cloned restriction fragment having homology with the DNA of an infecting T4 phage (for example, plasmid pVH691), the entire plasmid molecule can be recombined into a phage genome by the processes of this invention and subsequently replicated passively as part of a phage genome (supra). This passive replication of pBR322 DNA can be suppressed if the infecting phage particles are irradiated with ultraviolet light prior to infection. These effects are summarized in FIG. 8(C).

This data was obtained from a DNA-DNA hybridization experiment done as described supra (for the identification of denA mutant phage) except that 2 minute pulses of [$^3$H]-Thymidine (5 µCl/ml, 0.25 µmol/ml) were also given either before or at various times after infection of E. coli $B^E$-plasmid containing strains with phage mutant in gene 46 (amN130), the denA gene (S112), the D-region (SaΔ9) and in gene 23 (amA489). The phage were irradiated with a Westinghouse sterilamp 782L-30 to between $10^{-4}$ to $10^{-5}$ surviving plaque forming units. The $^3$H- and $^{14}$C-hybridization data obtained with nitrocellulose filters charged with 0.8ug of purified plasmid pBR322 DNA is presented as a ratio of $^3$H/$^{14}$C, is normalized to the $^3$H/$^{14}$C ratios obtained with uninfected cells samples and is plotted at the end point of each pulse period after phage infection.

In contrast to the results obtained with plasmid pVH691 (FIG. 8 [C]) UV irradiation of the infecting phage does not effectively block synthesis of plasmid pVH686 DNA (panel d). Plasmid pVH686 carries a restriction fragment containing parts of T4 genes 25 and y in addition to the gene 21–23 EcoRI restriction fragment carried in plasmid pVH691. The restriction fragment carrying parts of genes 25 and y clearly allows synthesis of plasmid vector DNA under conditions that block autonomous replication of pBR322 molecules (panel b) and that suppress said passive replication of pBR322 molecules containing cloned T4 DNA (panel c). The additional fragment of T4 DNA in plasmid pVH686 is thus acting as a functional origin of replication. The data in FIG. (8) is a control showing that the dose of UV irradiation given significantly reduces synthesis of phage DNA.

The block in pBR322 replication in T4 infected cells had previously been used by us as the basis for a method to screen for T4 restriction fragments that could act as a T4 origin of replication when cloned into pBR322. Thus, a large number of pBR322 derivatives containing cloned T4 restriction fragments were examined essentially as illustrated for plasmid pVH691. The clones screened included pKSK12 (H. M. Krisch and G. B. Selzer, "Construction and Properties of a Recombinant Plasmid containing gene 32 of Bacteriophage T4", J. Mol Biol 148: 199–218 (1981)) and pVH656 (supra). Both of these plasmids contain the T4 DNA in plasmid pVH672. If the infecting phage were not treated with ultraviolet irradiation, the amount of pBR322 DNA synthesized after phage infection was significantly greater with pKSK12 and pVH656 than with most other plasmids tested. Appropriate subcloning and further analysis with ultraviolet irradiated phage indicated that the origin of replication-like activity resided in the HindIII restriction fragment present in pVH672.

Figure 9:
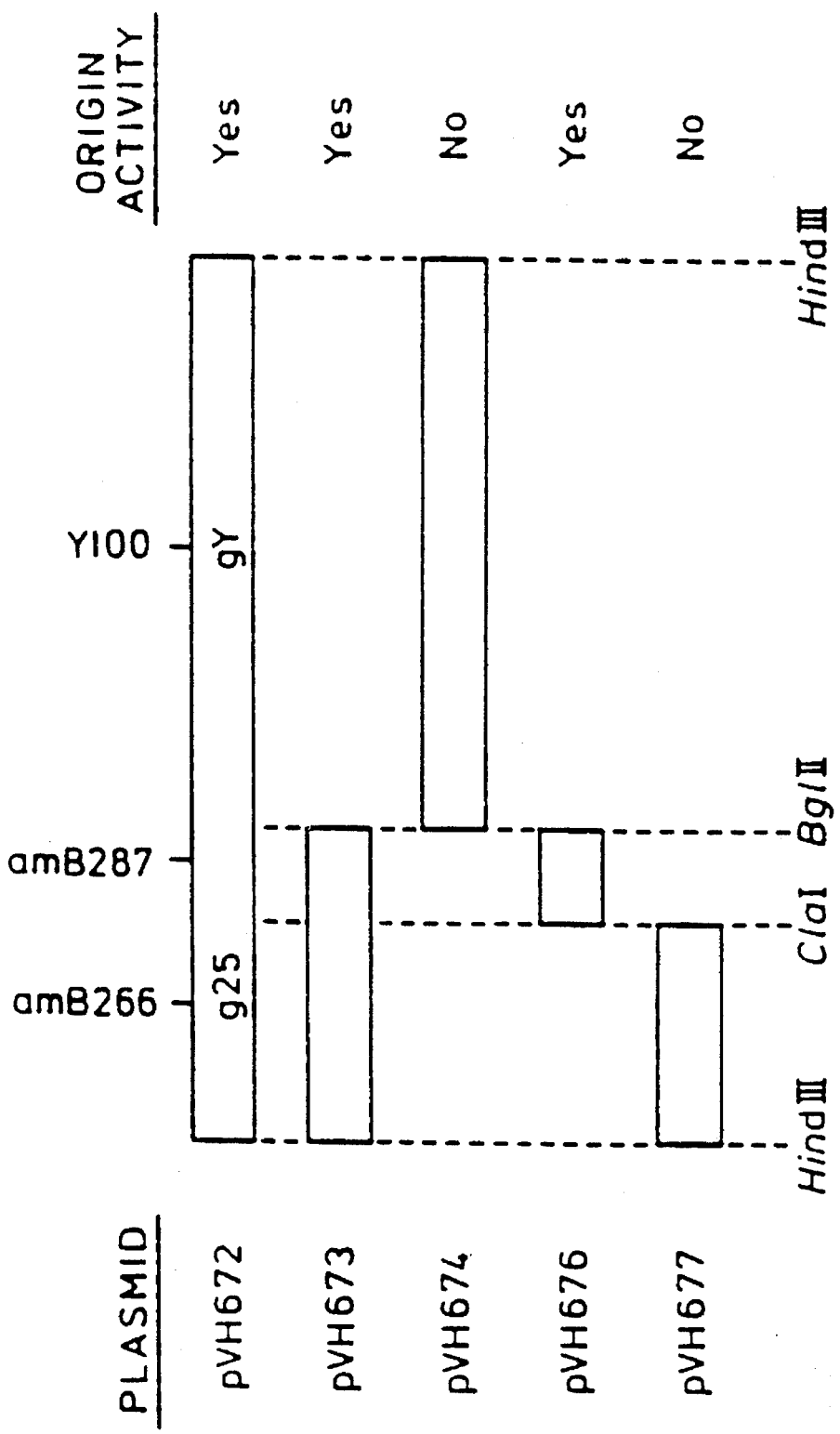
FIGS. 9A and 9B summarize the effects of different fragments of DNA from the T4 gene 25-y region on autonomous replication of pBE322 in T4 infected cells and present the nucleotide sequence of one of these restriction fragments.

Additional DNA-DNA hybridization of the type described allow a more precise mapping of the nucleotide sequence responsible for the origin of replication activity. The plasmids used for this mapping were derived from plasmid pVH672 DNA by digesting pVH672 and pBR322 DNAs with the restriction endonucleases cutting at the sites indicated in FIGS. 9A and 9B, or with BamHI in place of BglII, ligating the cut DNAs together in vitro with T4 DNA ligase, transforming competent cells and genetically identifying desired clones by their ability to give marker rescue for the markers indicated in FIGS. 9A and 9B as described above. The responsible sequence has been mapped to a 150 base pair BglII-ClaI restriction fragment. This restriction fragment, which can give marker rescue recombinants for the gene 25 mutant amB287 but not for the gene 25 mutant amB266, has been sequenced on both strands by the Maxim and Gilbert chemical sequencing method (Method. in Enzymol. (Acad. Press) Vol. 65 pp 499–560 (1980)). The results of the DNA-DNA hybridization experiments and the nucleic acid sequencing are summarized in FIGS. 9A and 9B.

Other evidence also indicates that most of the T4 gene 25 restriction fragment-dependent synthesis of pBR322 DNA detected in the DNA-DNA hybridization experiments represents DNA synthesized on autonomous plasmid molecules rather than said passive plasmid replication.

Total cellular DNA from T4 mutant (23amA489-46amN130-39amEA839-denAS112-denBSaΔ9) infected E coli $B^E$-pVH73 labelled from 7–9 minutes after infection as described (supra) was prepared for cesium density gradients as described (Mattson, T., Van Houwe, G. and Epstein, R. "Recombination between Bacteriophage T4 and plasmid pBR322 molecules containing cloned T4 DNA" J. Mol. Biol. 170:357–379 (1983), and centrifuged in cesium chloride-ethidium bromide density gradients (DNA from 6.10$^9$ infected cells was resuspended in 13 ml of TE, to which 2.6 ml of Ethidium bromide (3mg/ml) and 15.6 g of Cesium chloride were added and centrifuged for 60 hours at 35K. and 15 degrees in a Ti60 rotor).

Figure 10:
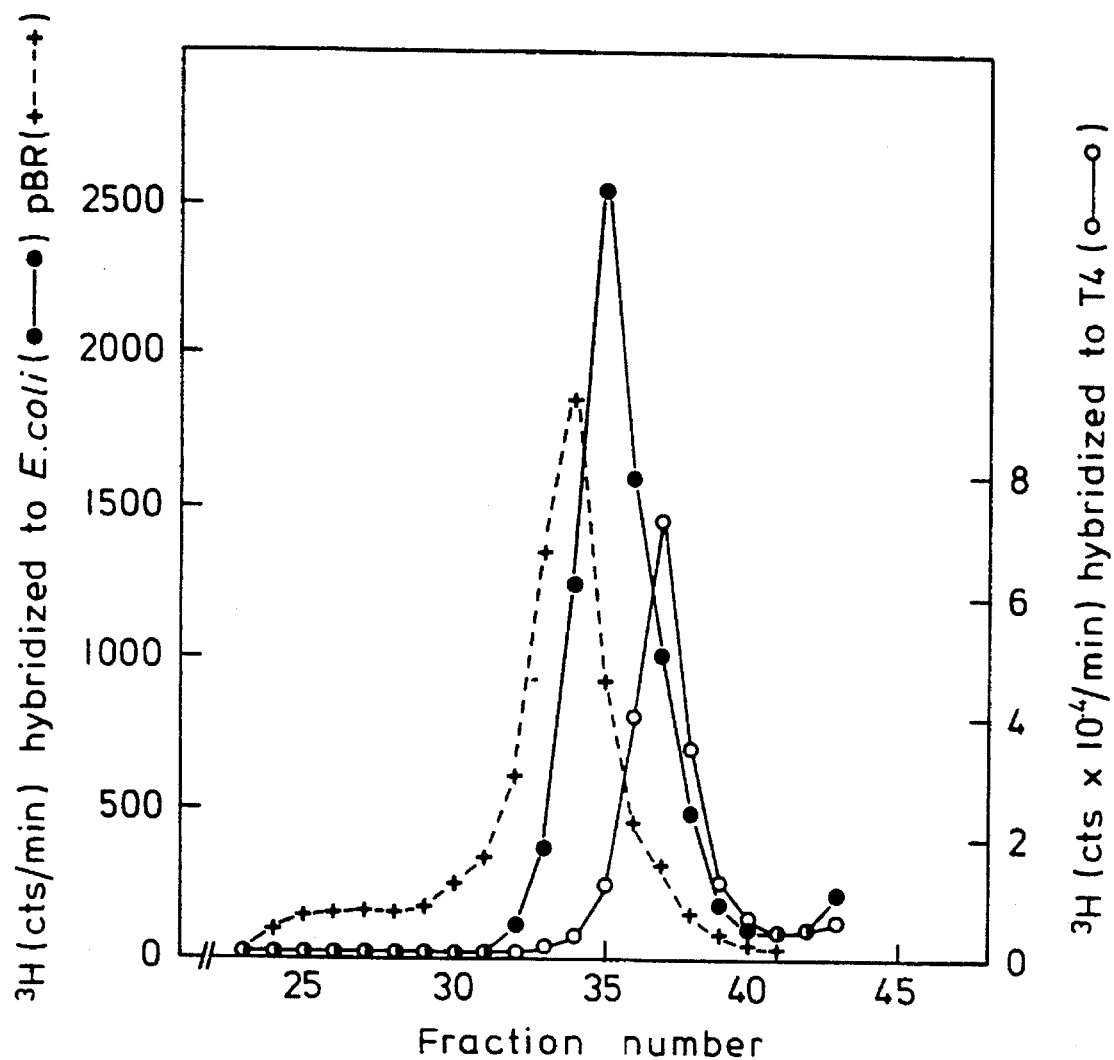
FIG. 10 shows the cesium chloride-ethidium bromide density gradient profiles of newly synthesized E. coli, pVH673 and T4 DNAs in T4 infected cells. The bottom of the gradient is on the left.

DNA-DNA hybridization analysis of individual fractions collected from the density gradients as described (Mattson et al. op. cit.) showed that the peak of radio-actively labelled pBR322 DNA banded in front of the peaks of radioactively labelled T4 and E. coli DNAs (FIG. 10).

Another kind of comparison between plasmids pVH691 and pVH686 provides additional evidence that the gene 25-y HindIII restriction fragment can act as a T4 origin of replication. This comparison is for the capacity to express cloned wild type gene 23 sequences under conditions that suppress said passive replication of plasmids as part of a phage genome. For this comparison we use the gene 46-23-denA-denB mutant phage described (supra) UV irradiated as described (supra) to infect E. coli $B^E$-pVH691 and $B^E$-pVH686, radioactively label newly synthesized proteins between 15–20 minutes after infection as described (supra) and analyse the labelled proteins on SDS-polyacrylamide gels as described (H. M. Krisch and G. B. Selzer, op. cit.).

Figure 11:
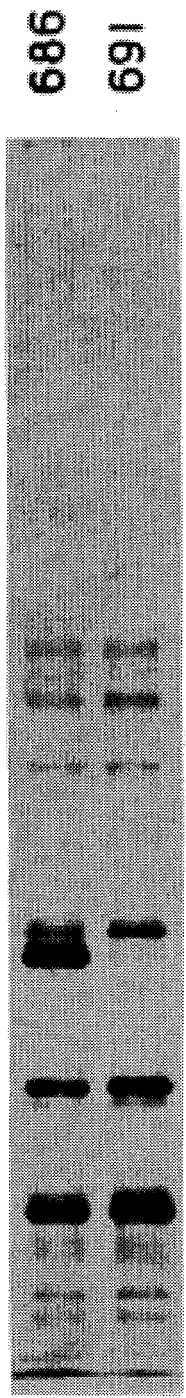
FIG. 11 presents as autoradiogram of the pattern of proteins synthesized when cells carrying plasmids pVH691 or pVH686 are infected with ultraviolet irradiated T4 phage particles. P23 points to the wild-type gene 23 protein band.
Figure 12A:
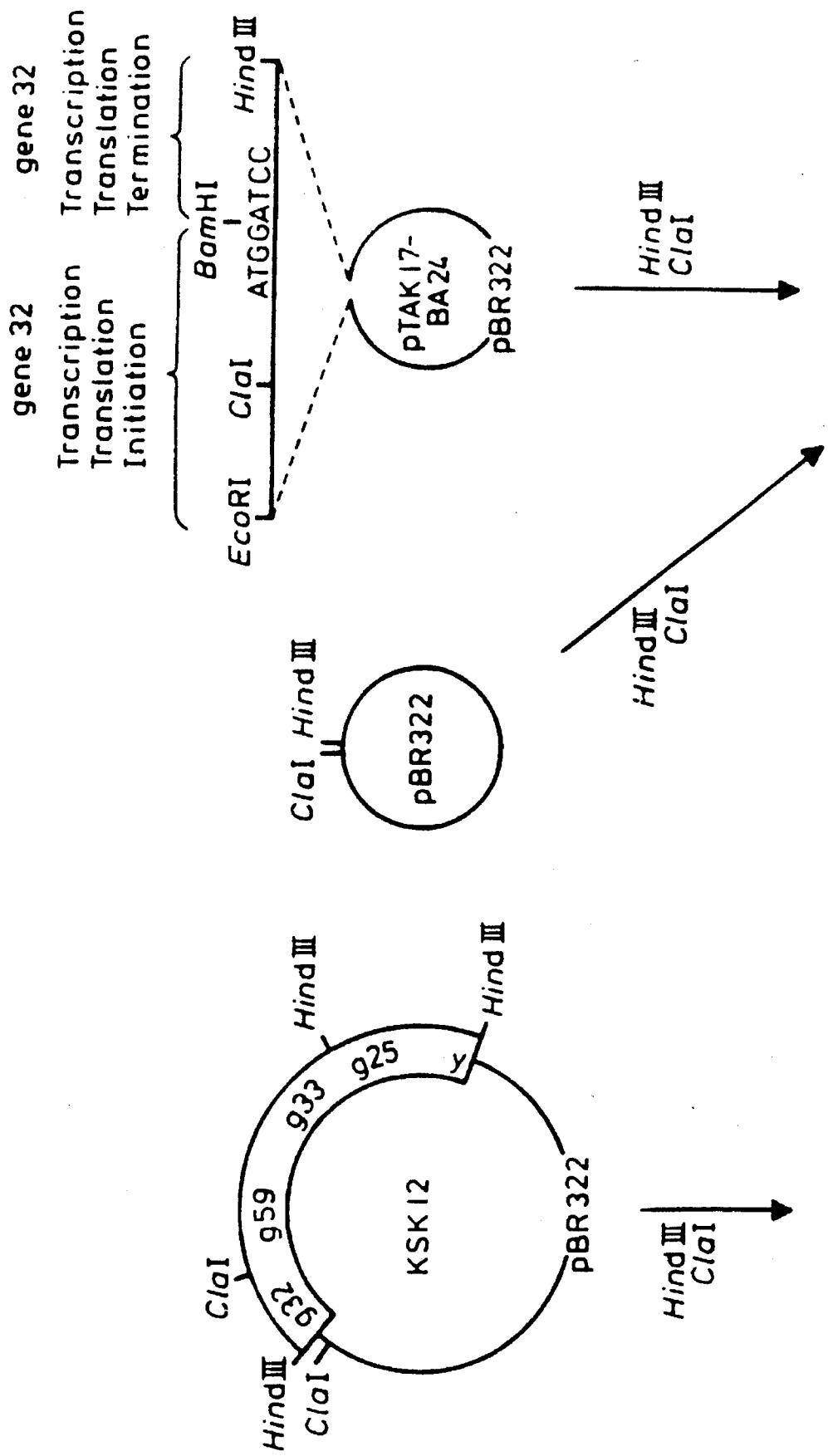
Figure 12B:
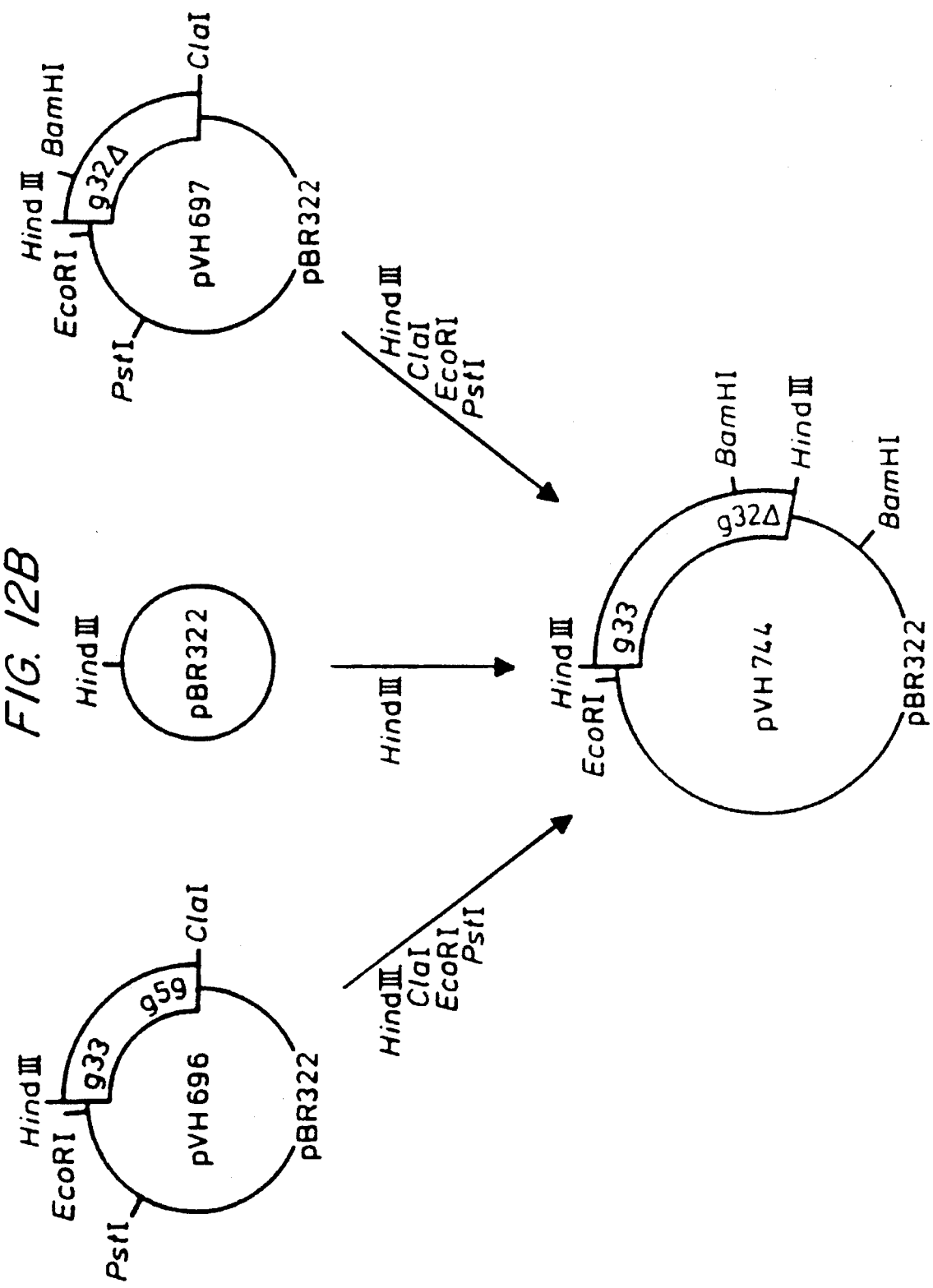
Figure 13C:
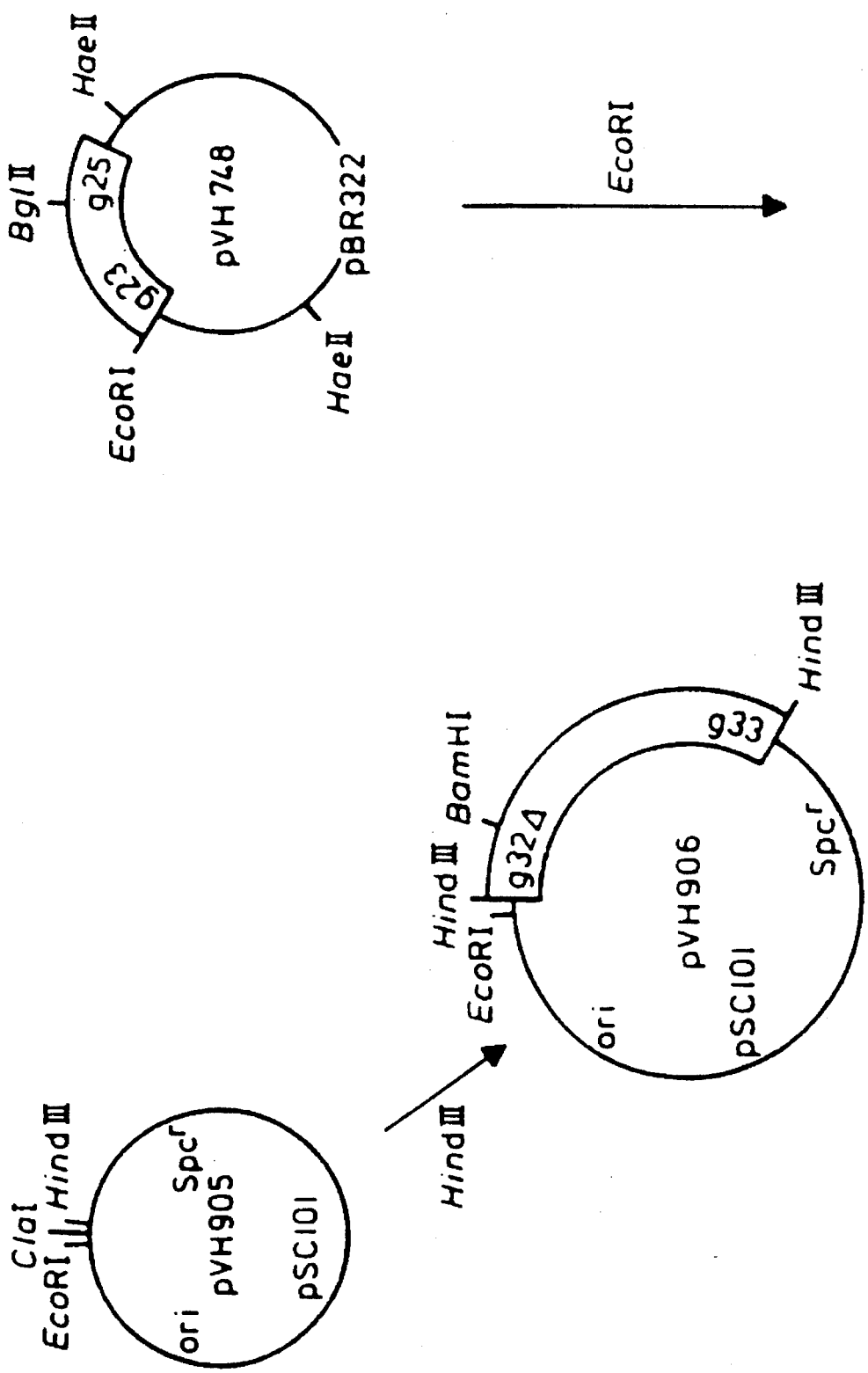
Figure 14:
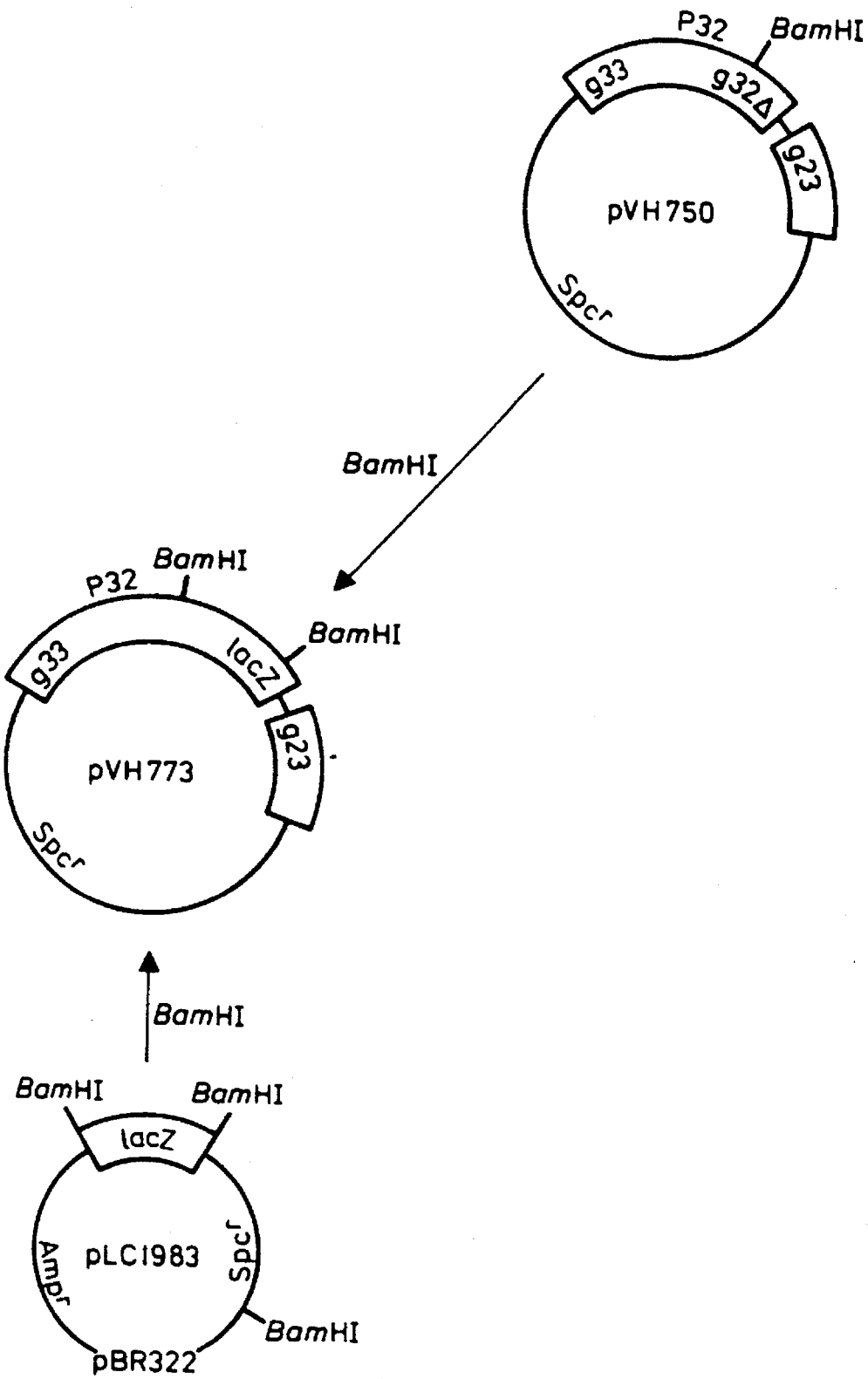
FIG. 14 summarizes the construction of plasmid pVH773.

This comparison (FIG. 11) shows at least 5 times more synthesis of gp23 from pVH686.

Increased expression of DNA cloned in pVH686 results from increased incorporation of the base hydroxymethylcytosine and from providing more of the replication required for normal gene 23 expression. Other pre-determined DNA sequences placed under the control of a T-even late gene expression control element would also be more efficiently expressed from a plasmid molecule containing the restriction fragment characterized as a T4 origin of replication.

This is the first reported instance of a cloned T4 restriction fragment acting as a T4 origin of replication.

The availability of a T4 restriction fragment characterized as a T4 origin of replication not only allows the replication and amplification of plasmid DNA in phage infected cells and aids in increasing the yield of the products of this invention (infra), it will also aid in furthering understanding of the molecular mechanisms of replication and can serve as a model for a systematic search of the T4 and other genomes for additional restriction fragments than can act in a similar manner.

INCREASING THE YIELD OF INVIABLE PHAGE PARTICLES CONTAINING CLONED DNA

Plasmid pVH686 prepared above was transformed into *E. coli* $B^E$ as described above. This plasmid containing $B^E$ strain is herein called $B^E$-pVH686.

A population of T4 phage particles was produced by infecting a culture of $B^E$-pVH686 at approximately $4.10^8$/ml with the T4 phage strain 23amA489-denA-SaΔ9 described above, at a multiplicity of infection of approximately five viable phage particles. The infected cells were incubated at 37° C., lysed by the addition of chloroform at approximately 60 minutes after infection, and the titres of viable phage particles containing the input gene 23 amber mutation and the wild type gene 23 allele derived from the cloned T4 DNA were determined. This lysate, which is herein called the first cycle lysate, was then used to infect a second culture of $B^E$-686 in a manner similar to that described for the infection of the first culture of $B^E$-pVH686. It must be emphasized that the multiplicities of infection of viable phage in the second and subsequent cycles of infection must be sufficient to insure that cells infected with an inviable contributor are also infected with a viable helper phage. This lysate, called the second cycle lysate, was in turn used to infect a third culture of $B^E$-pVH686 in a similar manner. This process which is herein called lysate cycling, was repeated a number of times. The populations of phage particles thus produced are related in that the $n^{th}$ lysate is the source of the input phage particles used to produce the n plus 1 lysate. These serially related lysates were analysed in three ways. A summary of the results of an analysis of the first, fifth and eight cycle lysates is given in Tables 4 and 5.

First, marker rescue frequencies among the viable progeny phage produced in the first, fifth and eighth cycle lysates were determined for a gene 23 marker. The results of these measurements are summarized in Table 4, column 1.

TABLE 4

| lysate number | marker rescue among viable phage | excess of inviable contributors over viable marker rescue |
|---|---|---|
| 1st cycle | 1.4% | 6.2-fold |
| 5th cycle | 13.5% | 4.2-fold |
| 8th cycle | 16.7% | 3.3-fold |

This marker rescue data was collected as described above for the data presented in Table 1. The marker rescue frequency in the first cycle lysate is low and not significantly different from the marker rescue frequencies given in Table 1. The level of marker rescue in the fifth cycle lysate is about 13 percent and is slightly greater than this in the eighth cycle lysate. Thus the marker rescue recombinants, which are viable phages are significantly less than 50 percent of the total viable phage.

Second, the levels of inviable contributor phage particles produced in the first, fifth and eighth cycles on $B^E$-pVH686 were determined and the results obtained are summarized in Table 4, column 2. This data was collected as described for the data presented in Table 2.

Inviable contributors can be detected in each of the cycled lysates. In each cycled lysate there are at least three times more inviable contributors than viable marker rescue recombinants. Consequently, in the 5th and 8th cycle lysates the total titres of inviable contributors are equal to approximately one half of the titre of the viable phage particles. If the number of viable phage produced in each cycled lysate was, for example, 100, then the number of inviable contributors would be about 50 for the 5th and 8th cycle lysates (13.5×4.2 and 16.7×3.3, respectively). The total number of phage particles (viable plus inviable) would be 150. The fraction of the total population of particles (150) that are inviable contributors (50) is thus about one-third or 33% in the 5th and 8th cycled lysates (50 divided by 150). In the present case the reiterated cycling process has resulted in about a five-fold enrichment for inviable contributors over the level present in the 1st cycle lysate.

Third, the average number of copies of T4 wild type gene 23 DNA in the first, fifth and eighth cycled lysates was determined (Table 5).

TABLE 5

| | molar ratio of wild type to mutant gene 23 polypeptides | molar ratio of wild type to mutant gene 23 DNA sequences | average number of copies of gene 23 in the phage population |
|---|---|---|---|
| INPUT PHAGE | — | 0 | 1 |
| 1st cycle lysate | 1.1 | 1.1 | 2.1 |
| 5th cycle lysate | 2.9 | 2.9 | 3.5 |
| 8th cycle lysate | 6.0 | 6.0 | 6.2 |

This was done by measuring the capacity of each of these lysates to synthesize gene 23 polypeptides as described above for FIG. 3. From the relative amounts of wild type and mutant gene 23 polypeptides (Table 5, column 1) one can directly determine the relative amounts of wild type and mutant copies of gene 23 DNA sequences (Table 5, column 2). From these ratios one can then calculate the average number of functional gene 23 sequences in the different lysates (Table 5, column 3). The calculations assume that the viable phage particles contain a single copy of gene 23, which is either wild type or mutant in the proportions indicated by marker rescue tests (Table 4) and that the inviable contributors, which are about one-third of the total progeny populations produced in the fifth and eighth cycles, contain a single mutant copy of gene 23 and a variable number of wild type gene 23 DNA sequences.

Numerous other plasmids suitable for producing and increasing the yield of the inviable contributor phage particles could also be constructed.

The particular DNA sequences used to create the DNA homology necessary for this invention are of course not limited to the T4 sequences in the gene 21–23 region but could be any DNA sequences present in the infecting phage genome.

EXAMPLE

INVIABLE T-EVEN PARTICLES AS EXPRESSION VECTORS

The process disclosed can be used to produce populations of inviable T-even phage particles having a number of unique properties. As an example of an application of the inviable particles so produced we describe the production of inviable particles capable of directing the synthesis of a non-T4 protein. Thus, we are showing how inviable T-even particles can be used as expression vectors.

These inviable particles will be called expression vector phage particles.

For this example we employ T4 gene 32 expression control elements. Of course many other T-even expression control elements or combinations of T-even expression control elements could also be used in expression vector phage particles. T-even expression control elements are preferred because expression of E. coli host genes is strongly blocked in T-even infected cells.

We first describe the construction of a plasmid that can be used to produce expression vector phage particles and then we describe the use of this plasmid to produce expression vector phage particles capable of expressing E. coli β-galactosidase DNA sequences.

CONSTRUCTION OF PLASMID pVH750

Plasmid pVH750 contains two independent replicons. One replicon (pVH748) provides elements allowing enrichment for inviable particles (supra), and the other replicon (pVH906) provides gene 32 expression control elements. This construction is summarized in FIGS. 12A–12C and 13A–13D.

CONSTRUCTION OF PLASMID pVH748

Plasmid pVH748 (FIGS. 13A–13D) is a derivative of pVH685. Plasmid pVH685 DNA differs from pVH686 DNA (supra) only in the orientations of the cloned T4 restriction fragments. Plasmid pVH685 was derived from plasmid pVH671 at the same time as and in exactly the same manner as pVH686 was derived from pVH672 (supra). Plasmid pVH685 has been modified so as to eliminate one of the two EcoRI recognition sites and the unique BamHI recognition site. Plasmid pVH685 DNA (ca. 2 µg) was digested to completion with BglII restriction endonuclease and then recircularized in vitro with T4 DNA ligase to form plasmid pVH693. Plasmid pVH693 DNA, digested with HaeII, was recircularized in vitro (ca. 0.1 µg) with T4 DNA ligase to form plasmid pVH748. Plasmid pVH748 has only two HaeII recognition sites, having deleted DNA between nucleotide coordinates 235 and 2351 of the pBR322 DNA sequence.

CONSTRUCTION OF PLASMID pVH906

Plasmid pVH906 is a derivative of plasmid pSC101 containing the pSC101 origin of replication, a spectinomycin drug resistance determinant and T4 DNA. The parts of plasmid pVH906 comprising the pSC101 origin of replication and the spectinomycin drug resistance determinant form plasmid pVH905. Plasmid pVH905 is a derivative of plasmid pGB2 (G. Churchward, D. Belin and Y. Nagamine. "A pSC101-derived plasmid which shows no sequence homology to other commonly used cloning vectors" Gene, in press), in which the EcoRI-HindIII region of pBR322 has been substituted for the EcoRI-HindIII poly-linker present in pGB2. This substitution, which eliminated the unique BamHI recognition site in pGB2, was accomplished by digesting plasmid pGB2 and pBR322 DNAs with HindIII, ligating them together in vitro (ca. 0.2 µg of each) with T4 DNA ligase, transforming competent E. coli cells and selecting for cells that were resistant to both spectinomycin and ampicillin. One such transformant contained plasmid pVH715. Plasmid pVH715 DNA digested with EcoRI was recircularized in vitro (ca. 0.1 µg) with T4 DNA ligase and used to transform competent E. coli. A spectinomycin resistant colony contained plasmid pVH905.

The T4 DNA component of plasmid pVH906 is on a HindIII restriction fragment obtained from plasmid pVH745.

CONTRUCTION OF PLASMID pVH745

The T4 DNA in plasmid pVH745 was obtained from the T4 DNA present in plasmid pKSK12 (H. M. Krisch and G. B. Selzer op. cit.) and from a gene 32 deletion derivative of pKSK12, pTAK17-BA24. Plasmid pTAK17-BA24 is a derivative of plasmid placB235 (H. M. Krisch and B. Allet. "Nucleotide sequence involved in bacteriophage T4 gene 32 translational self-control". Proc. Natl. Acad. Sci. (USA) 79:4937–4941 [1982]) containing a BamHI recognition site immediately after the ATG translation initiation codon and was obtained from H. M. Krisch. Plasmid pKSK12 DNA (ca. 2µg) was digested to completion with the restriction endonucleases ClaI and HindIII and then recircularized in vitro with T4 DNA ligase. One of the products of this ligation is plasmid pVH696, in which the HindIII-ClaI restriction fragment containing part of gene 33, gene 59 and the gene 59 proximal part of the gene 59-gene 32 intercistronic region has been subcloned into pBR322. Plasmid pTAK17-BA24 and pBR322 DNAs were digested to completion with ClaI and HindIII (pTAK-BA24 was also cut with PstI) and ligated together in vitro (0.5 to 2.0 µg of each) with T4 DNA ligase. One of the products of this ligation is plasmid pVH697 in which the HindIII-ClaI restriction fragment containing the gene 32 proximal part of the gene 59-gene 32 intercistronic region and the gene 32 transcription and translation termination signals have been subcloned into pBR322. Plasmid pVH697 is the only T4-pBR322 chimeric plasmid constructed here that was not initially identified by marker rescue (supra). It was identified only on the basis of restriction digest patterns. The cloned HindIII-ClaI restriction fragments from plasmids pVH696 and pVH697 were combined at their ClaI ends and cloned as a single HindIII restriction fragment into HindIII cut, alkaline phosphatase treated pBR322 in a single step by ligating together 0.3–1 µg of each digested DNA. The resulting plasmid pVH744, contains two BamHI recognition sites. In order to have a plasmid containing only the BamHI recognition site within the cloned T4 DNA, the HindIII restriction fragment in plasmid pVH744 was transferred into the unique HindIII restriction site of plasmid pVH699, by ligating HaeII plus HindIII cut pVH744 DNA (ca. 2 µg) with HindIII cut alkaline phosphatase treated pVH699 DNA (ca. 0.2µg), thus producing plasmid pVH745. Plasmid pVH699 is a derivative of plasmid pHP45Ω, (P. Prentki and H. M. Krisch. "In vitro insertional mutagenesis with a selectable DNA fragment". Gene, in press) that has been digested with EcoRI and recircularized in vitro (ca. 0.2 µg) with T4 DNA ligase in order to eliminate the two BamHI recognition sites in pHP45Ω.

The HindIII restriction fragment in pVH745 was cloned into the unique HindIII restriction site of plasmid pVH905, forming plasmid pVH906. Plasmid pVH906 and pVH748 DNAs were cut with EcoRI and ligated together (ca. 0.5 µg of each) to form plasmid pVH750.

Plasmid pVH750-contains a unique BamHI restriction site into which foreign DNA sequences can be inserted and expressed from T4 gene 32 control elements. The BamHI restriction site occurs immediately after the normal ATG translation initiation codon of gene 32. Most of the gene 32 coding sequences have been deleted although gene 32 transcription and translation termination signal are still present.

The sequence of nucleotides coding for the T4 gene 2 protein and more than 340 of the nucleotides at the 5' end and nearly 100 nucleotides at the 3' end of this gene has been determined (H. M. Krisch and B. Allet op. cit.) Nucleotide sequences near the 5' end of gene 32 have been shown capable of directing the in vitro synthesis of a fusion protein comprising gene 32 and β-galactosidase amino acids (H. M. Krisch and B. Allet op. cit.). The nucleotide sequences following the 3' end of the gene 32 coding region have been shown to act as a transcription termination signal in uninfected *E. coli* (P. Prentki and H. M. Krisch *op cit*).

Plasmid pVH750 can be used to produce expression vector phage particles (infra). Of course, many other T-even expression control elements could also be combined with a variety of restriction fragment allowing increased production of inviable contributor phage to produce a very large and diverse collection of plasmids similar to pVH750 in being suitable for producing expression vector phage particles.

T4 EXPRESSION VECTOR PHAGE

Plasmid pVH773 is a derivative of plasmid pVH750 in which a BamHI restriction fragment containing *E. coli* β-galactosidase coding sequences has been cloned in the proper orientation and translation reading frame for expression from the T4 control elements present in plasmid pVH750. Plasmid pVH773 was isolated following BamHI digestion of plasmid pVH750 and pLC1983 (P. Linder Ph.D. Thesis "Replication and Maintenance Functions of the Escherichia coli plasmid pSC101" Univ. of Geneva Department of Molecular Biology [1984]) DNAs, ligation of the digested DNAs (0.2–1 μg) together in vitro with T4 DNA ligase and transformation into *E. coli* strain LC1141 (P. Linder op cit) a recA derivative of MC1061(M. J. Casadaban, A. Martinez-Arias, S. K. Shapiro and J. Chou "δ-Galactosidase Gene Fusions for Analyzing Gene Expression in Escherichia coli and Yeast" Methods in Enzymol. (Acad. Press) Vol. 100 pp: 293–308 [1983]). pLC1983 is a derivative of pMC1403 (M. J. Casadaban et al. op cit) in which a second BamHI restriction site has been inserted adjacent to the AhaIII site located just beyond the end of lacZ. This BamHI restriction fragment can conveniently be moved into pVH750, forming pVH773, and identified among the blue colony when transformed LC1141 cells are spread on Xgal glucose minimal plates containing spectinomycin (100 μg/ml). The constructions of plasmids pVH750 and pVH773 are summarised in FIGS. 12A–12C, 13A–13D and 14.

T4 expression vector phage capable of directing the synthesis of enzymatically active β-galactosidase were produced by infecting a culture of strain LC1141-pVH773 at 30° with T4 phage containing two mutations in gene 23 (amA489 and amB17), a mutation in the denA gene (S112), a mutations in gene 32 (tsP7) and the deletion SaΔ9. Progeny phage particles produced after 90 minutes in LC1141-pVH773 and in the control strain LC1141-pVH750 (the first cycle lysates) were used to produce second cycle lysates at 30° as described (supra). The first and second cycle lysates produced in strains LC1141-pVH773 and LC1141-pVH750 were assayed for their capacity to synthesize β-galactosidase by using these lysates to infect strain MC1061 (supra) at 28° and at 40° and determining β-galactosidase activity according to the formula:

$$\text{UNITS} = 1000 \times \frac{OD_{420} - (1.75 \times OD_{550})}{t \times v \times OD_{600}}$$

as described (J. H. Miller "Experiments in Molecular Genetics" Cold Spring Harbor Laboratory (1972)).

Cells and phage in M9S media were mixed together at 28° and at 40°, and seven minutes later centrifuged, the pellet resuspended in room temperature media, centrifuged gain, resuspended again in room temperature media, centrifuged for a third time and finally resuspended in media at 28° or 40°, according to the temperature at the time of infection. (The washing process, which took about 30 minutes, was done to eliminate β-galactosidase activity present in the cycled lysates.) Control cultures, infected and washed in the presence of chloramphenicol (200 ug/ml) were treated in parallel and used for background substraction values. $OD_{600}$ readings were taken after the final resuspension and samples for enzymatic activity measurements were taken 30, 60 and 120 minutes after the final resuspension. Units of enzymatic activity detected after background substractions are given in Table 6.

TABLE 6

| 1st and 2nd cycle lysates from LC1141-plasmid | Units of β-galactosidase activity | | |
|---|---|---|---|
| | 30 | 60 | 120 |
| 28° C. 750-1st | 3 | 4 | 8 |
| 750-2nd | 3 | 4 | 11 |
| 773-1st | 42 | 75 | 129 |
| 773-2nd | 230 | 294 | 494 |
| 40° C. 750-1st | 2 | 4 | 10 |
| 750-2nd | 2 | 2 | 5 |
| 773-1st | 68 | 85 | 138 |
| 773-2nd | 325 | 529 | 1000 |

The data in Table 6 shows that phage particles produced in a first cycle lysate of *E. coli* strain LC1141-pVH733 are capable of directing the synthesis of an enzymatically active non-T4 protein. This capacity is increased by producing a second cycle lysate and this capacity is greater at 40° than at 28°. This is the result expected if the synthesis of β-galactosidase activity is under the control of gene 32 expression control sequences. Finally, the level of galactosidase activity can accumulate for at least two hours. In contrast, the capacities of the first and second cycle lysates produced on LC1411-pVH750 to produce β-galactosidase are very low.

Bacterial strain *E. coli* $B^E$ containing plasmid pVH686 was deposited on Sep. 2, 1983 at the Agriculture Research Culture Collection (NRRL), Peoria, Ill., with accession no. NRRL B-15583. *E. coli* strain LCl141 containing plasmid pVH773 was deposited at NRRL on Sep. 7, 1984, with accession no. NRRL B-15876.

We claim:

1. A method of producing a phage-infected host bacterium, for obtaining products including a population of inviable T-even bacteriophage particles containing DNA of a predetermined non-T-even base sequence and DNA thereof, and for expressing a protein encoded by a predetermined non-T-even base sequence, the method comprising:

infecting a host bacterium containing a replicon having a predetermined non-T-even base sequence with a T-even phage, said replicon also containing a DNA sequence sufficiently homologous to a DNA sequence in the T-even phage to allow recombination between the replicon and phage DNA to take place, said T-even phage having inactive wild type denB gene functions, and recovering the phage-infected host bacterium containing the predetermined non-T-even base sequence.

2. A method as recited in claim 1, wherein the host bacterium blocks the wild type denB gene functions to inactivate the wild type denB gene of the T-even phage.

3. A method as recited in claim 1, wherein said T-even phage carries one or more mutations which abolish all functions of the wild type denB gene to inactivate the wild type denB gene of the T-even phage.

4. A method as recited in claim 1, wherein the host bacterium is *E. coli*.

5. A method as recited in claim 1, wherein the T-even phage is bacteriophage T4.

6. A method as recited in claim 1, wherein the T-even phage is a T4 mutant carrying deletion SAΔ9.

7. A method as recited in claim 1, wherein said replicon further contains a DNA sequence, expression of which results in an increase in the yield of said population of inviable T-even bacteriophage particles containing DNA of a predetermined non-T-even base sequence relative to the yield obtained when said replicon lacks the DNA sequence.

8. A method as recited in claim 7, further comprising performing an enrichment process after the infecting step, wherein the enrichment process includes the following cycle: lysing the host bacterium cell to obtain lysate phage particles, and reinfecting a subsequent cell of said host bacterium with the lysate phage particles.

9. A method as recited in claim 8, further comprising repeating said cycle at least once, wherein in each subsequent cycle the lysate phage particles of the reinfected host bacterium from the preceding cycle provide the reinfecting phage for the subsequent cell of the host bacterium.

10. A method as recited in claim 1, further comprising obtaining from the phage-infected host bacterium, inviable T-even bacteriophage particles which contain copies of said predetermined non-T-even base sequence.

11. A method as recited in claim 10, further comprising incorporating copies of said replicon in tandem arrangement into the DNA of said infecting T-even phage.

12. A method as recited in claim 1, wherein said predetermined non-T-even base sequence encodes for a protein.

13. A method as recited in claim 12, further comprising: obtaining a population of phage particles from the phage-infected host bacterium, and infecting fresh host bacterium cells with the population of phage particles to enable expression and production of the protein.

14. A method as recited in claim 12, further comprising isolating the protein from products of the phage-infected host bacterium.

15. A method as recited in claim 1, further comprising isolating a polynucleotide which is transcribed from said predetermined non-T-even base sequence from products of the phage-infected host bacterium.

16. A method as recited in claim 1, further comprising obtaining from the phage-infected bacterium, inviable T-even bacteriophage particles containing DNA of the predetermined non-T-even base sequence under control of a T-even expression control sequence.

17. A method as recited in claim 1, further comprising isolating a sequence of DNA different than said predetermined non-T-even base sequence from products of the phage-infected host bacterium.

18. A method as recited in claim 1, wherein the recombined replicon and phage are employed to replicate, transcribe or translate products therefrom.

19. A method as recited in claim 1, further comprising isolating said predetermined non-T-even base sequence from the phage infected host bacterium.

20. A method as recited in claim 1, wherein the replicated, transcribed or translated products are isolated from the host bacterium.

21. A method as recited in claim 1, wherein the replicon of the host bacterium contains an origin of replication that allows autonomous replication of plasmid pBR322 in *E. coli* when infected with T-even phage.

22. A method as recited in claim 21, wherein said origin of replication that allows autonomous replication of plasmid pBR322 in *E. coli* when infected with T-even phage is located between kilobase coordinates 114.00 and 114.15 on a map of the T4 genome.

* * * * *